US010370409B2

(12) United States Patent
Kodadek et al.

(10) Patent No.: US 10,370,409 B2
(45) Date of Patent: Aug. 6, 2019

(54) SYNTHESIS OF LIBRARIES OF PEPTIDE TERTIARY AMIDES

(71) Applicant: The Scripps Research Institute, La Jolla, CA (US)

(72) Inventors: Thomas Kodadek, Jupiter, FL (US); Yu Gao, Jupiter, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/354,031

(22) PCT Filed: Oct. 25, 2012

(86) PCT No.: PCT/US2012/061963
§ 371 (c)(1),
(2) Date: Apr. 24, 2014

(87) PCT Pub. No.: WO2013/063296
PCT Pub. Date: May 2, 2013

(65) Prior Publication Data
US 2014/0315831 A1   Oct. 23, 2014

Related U.S. Application Data

(60) Provisional application No. 61/551,110, filed on Oct. 25, 2011.

(51) Int. Cl.
*A61K 38/00* (2006.01)
*C07K 7/06* (2006.01)
*C07C 231/02* (2006.01)
*C07K 1/04* (2006.01)
*C07C 51/363* (2006.01)
*A61K 38/08* (2019.01)
*C07K 5/062* (2006.01)
*C07K 5/083* (2006.01)
*G01N 33/68* (2006.01)
*C07K 14/00* (2006.01)

(52) U.S. Cl.
CPC ............... *C07K 7/06* (2013.01); *A61K 38/08* (2013.01); *C07C 51/363* (2013.01); *C07C 231/02* (2013.01); *C07K 1/042* (2013.01); *C07K 1/047* (2013.01); *C07K 5/06026* (2013.01); *C07K 5/0806* (2013.01); *C07K 14/001* (2013.01); *G01N 33/6845* (2013.01)

(58) Field of Classification Search
None
See application file for complete search history.

(56) References Cited

U.S. PATENT DOCUMENTS

| 5,555,889 | A | 9/1996 | Karagueuzian et al. |
| 5,977,301 | A | 11/1999 | Zuckerman et al. |
| 8,748,388 | B2* | 6/2014 | Tulla-Puche ............. C07K 7/56 514/183 |
| 2003/0013126 | A1 | 1/2003 | Singh et al. |
| 2004/0161798 | A1 | 8/2004 | Kodadek |
| 2008/0227109 | A1 | 9/2008 | Chen et al. |
| 2008/0269305 | A1* | 10/2008 | Allegretti et al. ............. 514/381 |
| 2010/0158814 | A1 | 6/2010 | Bussat et al. |
| 2011/0054146 | A1 | 3/2011 | Ponnusamy |

FOREIGN PATENT DOCUMENTS

| WO | WO2002081637 | 8/2004 |
| WO | WO2007117404 | 10/2007 |

OTHER PUBLICATIONS

Moumne, R., et al, "Efficient Synthesis of 2-Amino Acid Homologation of-Amino Acids Involving the Reformatsky Reaction and Mannich-Type Iminium Electrophile," Journal of Organic Chemistry (2006), 71 (8), 3332-3334 .*
Simon, R. et al, "Peptoids: a modular approach to drug discovery", Proc. Natl. Acad. Sci., USA, vol. 89, pp. 9367-9371, (Oct. 1992).
Yamagami, J. et al, "Homologous regions of autoantibody heavy chain complementarity-determining region 3 (-CDR3) in patients with pemphigus cause pathogenicity", The Journal of Clinical Investigation, vol. 120, pp. 4111-4117, (2010).

* cited by examiner

Primary Examiner — Thomas S Heard
(74) Attorney, Agent, or Firm — Schwegman Lundberg & Woessner, P.A.

(57) ABSTRACT

The present disclosure is directed to a novel class of peptide-like oligomers called peptide tertiary amides (PTAs) and a combinatorial library of PTAs along with synthetic routes for the preparation of large combinatorial libraries of these compounds. The peptide tertiary amides provide an exceptional source of high affinity and selective protein ligands that are useful as tools for biological research and as drug leads, among others.

11 Claims, 12 Drawing Sheets

FIG. 1. Structural Comparison Among N-Methylated Peptide, Peptoid, and PTA
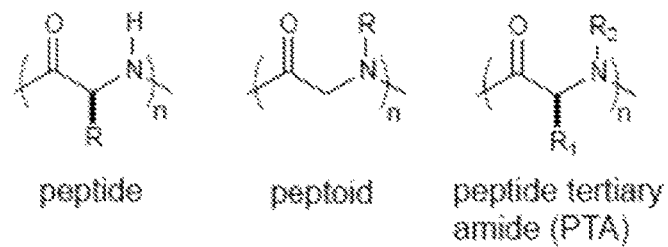

FIG. 2A. General Preparation of PTA Building Blocks from Natural Amino Acids
a.
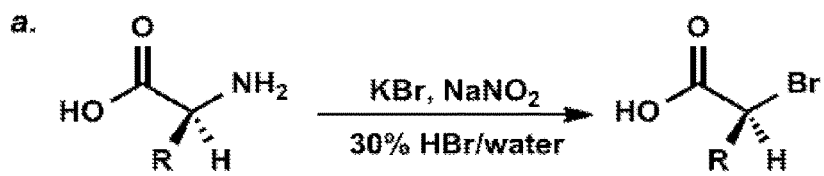
R= side chains from amino acids such as: Ala, Phe, Val, Leu, Ile, Ser, Thr, Glu, Asp etc. 64%~87% overall yield

FIG. 2B. Use of PTA Building Blocks in Peptoid Sub-Monomer Synthesis
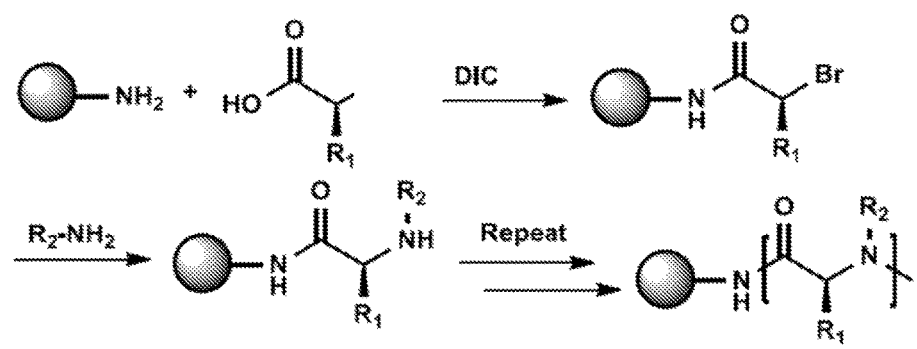

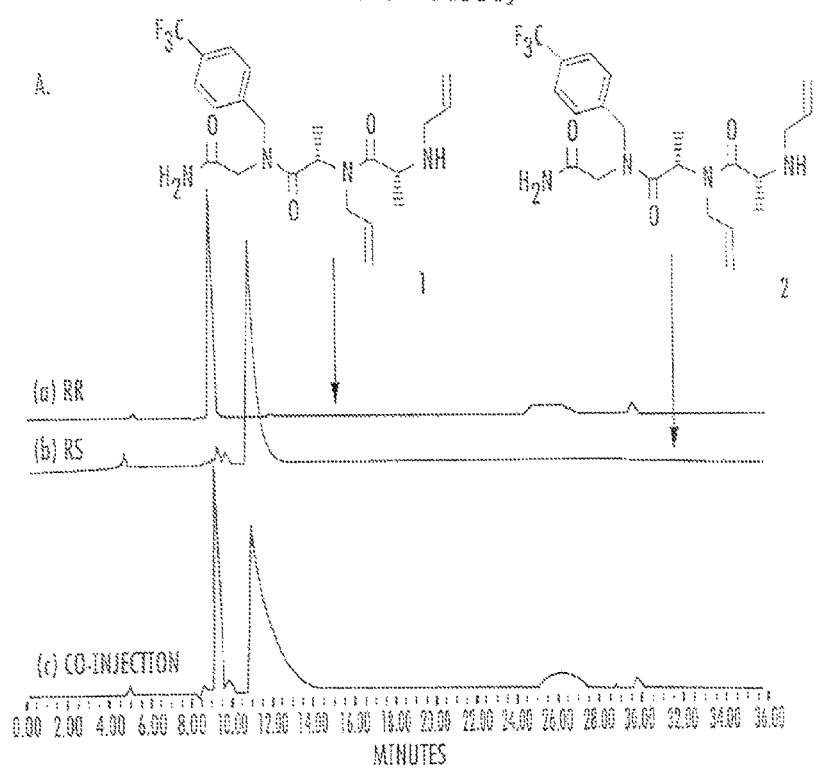
FIG. 4A. No Loss of Stereochemical Purity

FIG. 4B. Little to No Racemization During Synthesis
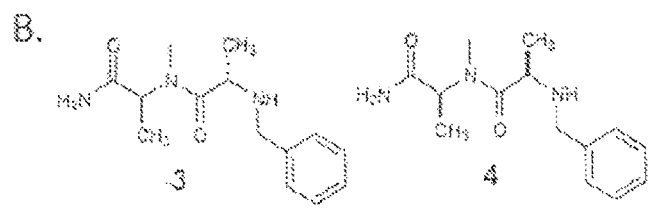

FIG. 4C. Synthesis of D$_5$-L-Alanine
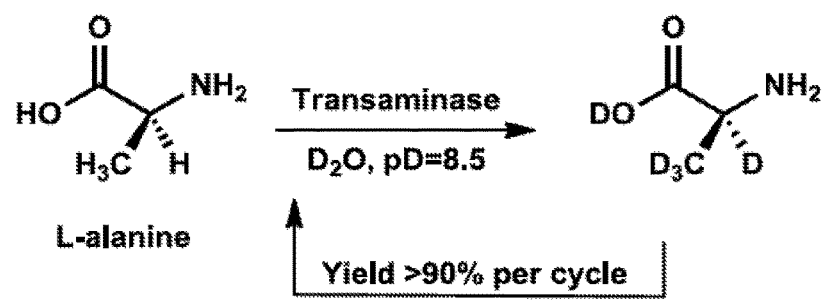

A.

B.

SYNTHESIS OF LIBRARIES OF PEPTIDE TERTIARY AMIDES

CROSS-REFERENCE TO RELATED APPLICATIONS

This application is a national stage filing in accordance with 35 U.S.C. § 371 of PCT/US2012/061963, filed Oct. 25, 2012, which claims the benefit of U.S. Provisional Application No. 61/551,110, filed Oct. 25, 2011, which the contents of each application are expressly incorporated by reference herein in their entirety.

STATEMENT OF FEDERAL FUNDING

This invention was made with government support under Contract No. OD000663 awarded by the National Institutes of Health. The government has certain rights in this invention.

FIELD OF THE INVENTION

Embodiments are provided that are directed to synthetic processes for making peptide-like oligomers, and resulting peptide-like oligomers. The peptide-like oligomers have can have various substituents, which can result in diverse combinatorial libraries.

BACKGROUND

N-methylated peptides have attracted considerable attention from chemists because of their improved cell permeability and stability relative to peptides and their appearance in a host of bioactive natural products. At the other end of the spectrum are peptoids, in which diverse groups are appended to the main chain nitrogen, but the amino acid unit is always glycine (Simon, et al., *Proc. Natl. Acad. Sci. USA* 1992, 89, 9367-71).

N-methylated peptides, however, are restricted to only a methyl substituent on the nitrogen atom, and thus, are impractical for the creation of large, diverse combinatorial libraries.

One bead one compound (OBOC) libraries of peptoids (oligo-N-substituted glycines) have been shown to be an excellent source of selective protein ligands. Peptoids are almost ideal molecules for library construction via split and pool synthesis since they are synthesized via a protocol that allows cheap, readily available primary amines to be employed as diversity elements. Moreover, peptoid structures can be deduced readily by tandem mass spectrometry, eliminating the need for library encoding. Finally, the absence of the highly polar and well-hydrated backbone N—H bonds renders peptoids far more cell permeable than peptides, which is important for targeting intracellular proteins. However, there have been few reports of high affinity peptoid-protein interactions with $K_D$ values in the low nM range, which is highly desirable in a drug lead or in a tool compound. Without being bound by any theory, it is likely that this is due, at least in part, to the inherent "floppiness" of peptoids. In most cases, the cis and trans amide bond isomers are close to one another in energy and so peptoids exist as a complicated mixture of these conformational isomers. Moreover, there is little obstruction in rotation about both the carbonyl-Cα and the Cα-nitrogen bonds. Assuming that protein-binding peptoids assume a particular conformation upon binding to their target, this means that a large entropic penalty must be paid, which will limit affinity. Several laboratories have reported approaches to controlling the amide bond geometry in peptoids, but these approaches are not readily applicable to the synthesis of large, high-quality combinatorial libraries. These approaches do not significantly address the issue of restricting rotation about the carbonyl-Cα and the Cα-nitrogen bonds.

SUMMARY

This Summary is provided to present a summary to briefly indicate the nature and substance of the present disclosure. It is submitted with the understanding that it will not be used to interpret or limit the scope or meaning of the claims.

In some embodiments, the present disclosure provides a novel class of peptide-like oligomers called peptide tertiary amides (PTAs). In some embodiments, synthetic routes are provided for the preparation of large combinatorial libraries of these compounds. With restricted conformations, the peptide tertiary amides in this disclosure provide an exceptional source of high affinity and selective protein ligands that can be used as tools for biological research and as drug leads, among others.

One aspect is directed to peptide tertiary amides of the following general formula (I):

(I)

wherein $R_1$ and $R_2$ are independently selected from H, optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, optionally substituted alkoxyl, optionally substituted heteroaryl, optionally arylalkoxyl, optionally substituted acyl, OH, OR', $NH_2$, NHR', $NR'_2$, SH, SR', C(O)R', or an amino acid side chain, along with any stereoisomeric, tautomeric, or polymeric form thereof.

wherein R' is selected from optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, or optionally substituted acyl.

In some embodiments, at least one of $R_1$ and $R_2$ is an amino acid side chain. In some embodiments, the PTA comprises isotopic labeling.

In another aspect, the present disclosure provides a method or process for making a PTA as described. In accordance with some embodiments, the process comprises the following steps. The first step comprises oxidizing a primary amine of an amino acid of formula (II) with an oxidizing agent followed by treatment with a nucleophilic bromide source to give an optically pure 2-bromo acid of formula (III), according to Scheme A. An example of a 2-bromo acid is 2-bromoacetic acid.

Scheme A

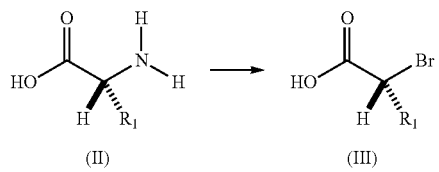

(II) → (III)

The second step comprises treating the 2-bromo acid of formula (III) with an amine of formula (IV) to produce the peptide tertiary amide of formula (I), according to Scheme B.

Scheme B

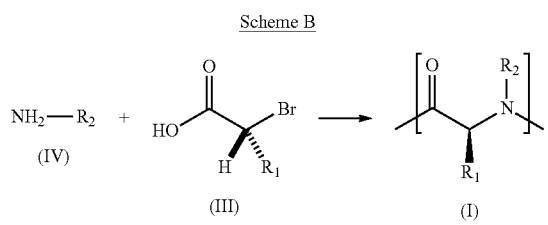

(IV) + (III) → (I)

For example, the oxidizing agent comprises one of nitrous acid and sulfuric acid in some embodiments. Bromide source can comprise a chemical selected from the group consisting of potassium bromide, hydrogen bromide, and sodium bromide. In some embodiments, the amine of formula (IV) is a primary amine. In some embodiments, the peptide tertiary amide (PTA) comprises one or more Cα- and N-substitutions. The PTA is optically (or enantiomerically or chirally) pure with a certain configuration in accordance with some embodiments. In some embodiments, the peptide tertiary amide comprises at least 90% enantiomeric excess of the (R) enantiomer. In some other embodiments, the peptide tertiary amide comprises at least 90% enantiomeric excess of the (S) enantiomer.

In some embodiments, the method or process for making the PTAs comprises a solid or semi-solid phase synthetic step, for example, using a bead, according to Scheme C. In some embodiments, the first step comprises bonding a chiral 2-bromoacid of formula (III) onto the sold-phase bead using a coupling agent in an appropriate solvent to give a compound of formula (V). In some embodiments, the solid-phase comprises a bead having a cleavable linker. In some embodiments, the cleavable linker is selected from, but not limited to, naturally occurring and synthetic α, β, γ, or δ amino acids, for example, methionine. In some embodiments, the coupling agent, for example, can be diisopropylcarbodiimide (DIC). In some embodiments, the solvent is N,N-dimethylformamide.

The second step comprises reacting the compound of formula (V) with an amine functionalized bead or an amine of formula (IV) to give a compound of formula (VI). In some embodiments, the amine of formula (IV) is a primary amine. The compound of formula (VI) is further reacted with additional 2-bromo acid of formula (III) followed by amine of formula (IV) to obtain oligomers of the compound of formula (VI). In some embodiments, the oligomers of the compound of formula (VI) are released from the bead by cleaving the oligomers from the solid-phase bead. In such cleavage reaction, the bound oligomer is reacted with a chemical, for example, cyanogen bromide.

Scheme C

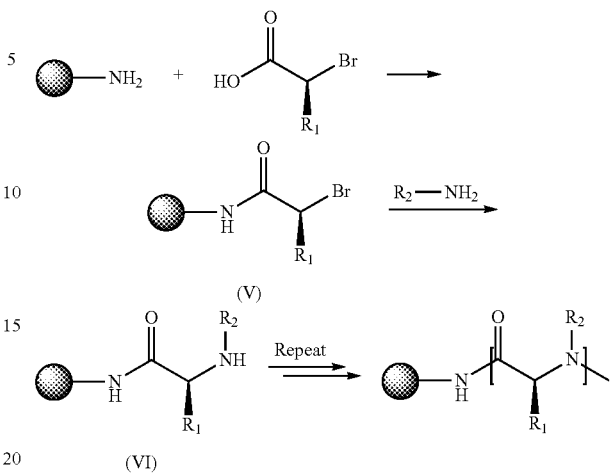

In some embodiments, the peptide tertiary amide (PTA) comprises one or more Cα- and N-substitutions. The PTA is optically or chirally pure with a certain configuration in accordance with some embodiments.

The present disclosure also provides a combinatorial library of compounds comprising a plurality of molecules of peptide tertiary amide (PTA) each having at least one unit of formula (I). In some embodiments, at least one of $R_1$ and $R_2$ is an amino acid side chain. In some embodiments, the PTA comprises isotopic labeling. In some embodiments, each of the plurality of molecules of PTA has at least two, for example, three, four, five or six units, of formula (I).

BRIEF DESCRIPTION OF THE DRAWINGS

FIG. 1 is a scheme illustrating the structural differences between N-methylated peptides, peptoids and PTAs.

FIG. 2A is a non-limiting reaction scheme showing the preparation of PTA building blocks from natural amino acids in accordance with some embodiments.

FIG. 2B is a non-limiting reaction scheme showing the use of PTA building blocks in a peptoid synthesis in accordance with some embodiments.

FIG. 4A shows two exemplary compounds without loss of stereochemical purity in accordance with some embodiments.

FIG. 4B shows two exemplary compounds with little or no racemization during synthesis in accordance with some embodiments.

FIG. 4C is a reaction scheme showing the synthesis of $D_5$-L-alanine in accordance with some embodiments.

DETAILED DESCRIPTION

Figure 3:
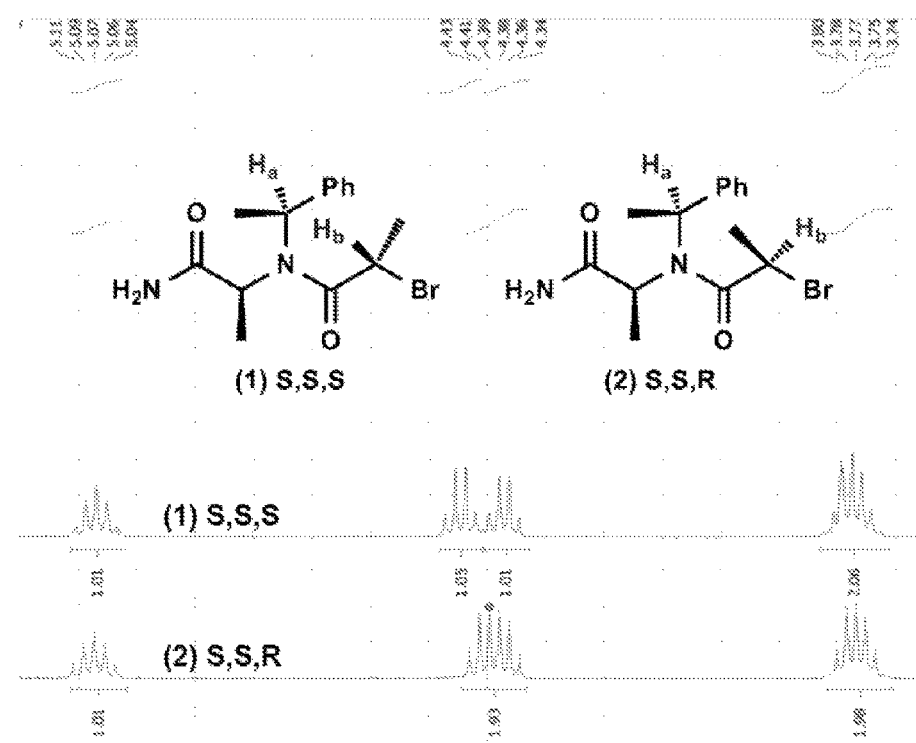
FIG. 3 shows a crude $^1$H NMR spectrum of two diastereomers synthesized using diisopropylcarbodiimide (DIC) in accordance with some embodiments.

In some embodiments, a novel class of peptide-like oligomers called peptide tertiary amides (PTAs) is provided. In some embodiments, synthetic routes for the preparation of large combinatorial libraries of these compounds are provided. The peptide tertiary amides can provide an exceptional source of high affinity and selective protein ligands that can be used, for example, but not limited to, as tools for biological research and as drug leads, among others.

I. Peptide Tertiary Amides:

There is a need in the art for a facile route to large, high-quality combinatorial libraries of peptide-like oligomers that combine the desirable attributes of N-methylated peptides and peptoids that also possess restricted rotation about the carbonyl-Cα and the Cα-nitrogen bonds in order to maximize protein interactions.

One aspect of the invention is directed to peptide tertiary amides of the following general formula (I):

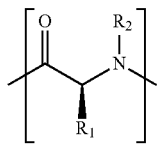

(I)

wherein $R_1$ and $R_2$ are independently selected from H, optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, optionally substituted alkoxyl, optionally substituted heteroaryl, optionally arylalkoxyl, optionally substituted acyl, OH, OR', $NH_2$, NHR', $NR'_2$, SH, SR', C(O)R', or an amino acid side chain, along with any stereoisomeric, tautomeric, or polymeric form thereof.

wherein R' is selected from optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, or optionally substituted acyl.

General formula (I) is shown for the purpose of illustration only. It is not limited to certain chirality only. For example, the chiral center at the carbon atom (Cα) which $R_1$ is connected with can be in R-configuration in some embodiments, and can be in S-configuration in other embodiments. In some embodiments, the peptide tertiary amides (PTAs) can include N-methylated peptides or peptoid (FIG. 1).

In some embodiments, the peptide tertiary amides may comprise monomers as well as oligomers. The oligomers, for example, may comprise, but are not limited to, dimers, trimers, and tetramers. The oligomers may also comprise homo-oligomers as well as hetero-oligomers.

The length of the oligomers can vary. Depending on the use, the oligomers of the peptide tertiary amides of the present invention may also vary in length. The desired length can be determined by and made by one of skill in the art in view of the disclosure provided herein.

In some embodiments, the peptide tertiary amide (PTA) comprises one or more Cα- and N-substitutions. The PTA is optically or chirally pure with a certain configuration in accordance with some embodiments. With respect to a certain carbon atom, in some embodiments, the peptide tertiary amide comprises at least 90% enantiomeric excess of the (R) enantiomer. In some other embodiments, the peptide tertiary amide comprises at least 90% enantiomeric excess of the (S) enantiomer. In some embodiments, the PTA is made through a sub-monomer synthesis route. In some embodiments, the PTA is synthesized through a semi-solid or solid-phase sub-monomer synthesis route.

II. Preparation of the Peptide Tertiary Amides:

In another aspect, the present disclosure provides a method or process for making PTAs. In some embodiments, such a process is a sub-monomer synthesis. In some embodiments, methods of solid phase or semi-solid phase synthesis of the peptide tertiary amides of formula (I) are provided.

In some embodiments, a method for a synthetic route to an optically pure 2-bromo acid building block of the peptide tertiary amides of formula (I) are provided.

For example, in some embodiments, the primary amine of a compound of formula (II)

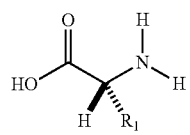

(II)

is treated with an oxidizing agent. In some embodiments, the method comprises treating the oxidized molecule from the preceding step with a nucleophilic bromide source to give an optically pure 2-bromo acid of formula (III):

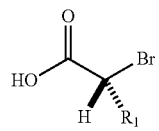

(III)

wherein $R_1$ is selected from H, optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, optionally substituted alkaryl, optionally substituted alkoxyl, optionally substituted heteroaryl, optionally arylalkoxyl, optionally substituted acyl, OH, OR', $NH_2$, NHR', $NR'_2$, SH, SR', C(O)R', or an amino acid side chain, along with any stereoisomeric, tautomeric, or polymeric form thereof.

wherein R' is selected from optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, or optionally substituted acyl.

General formula (II) and (III) are shown for the purpose of illustration only. Formula (II) or (III) is not limited to certain chirality only. For example, the chiral center at the carbon atom (Cα) which R1 is connected with can be in R-configuration in some embodiments, and can be in S-configuration in other embodiments.

In some embodiments, the oxidizing agent is, but not limited to, nitrous acid/sulfuric acid and sodium nitrite/hydrobromic acid. In some embodiments, the oxidizing agent comprises one of nitrous acid and sulfuric acid.

In some embodiments, the nucleophilic bromide source is, but not limited to, potassium bromide, hydrogen bromide, sodium bromide, or combination thereof. In some embodiments, the bromide source can comprise a chemical selected from the group consisting of potassium bromide, hydrogen bromide, and sodium bromide. In some embodiments, the nucleophilic bromide source is potassium bromide.

In addition to the oxidizing agents and nucleophilic bromide sources described herein, other oxidizing agents and bromide sources can be used. For example, oxidizing agents and nucleophilic bromide sources that can also be used are disclosed in COMPREHENSIVE ORGANIC SYNTHESIS, Richard Larock, (1999), which is incorporated herein by reference.

In some embodiments, the method comprises a step, such as, but not limited to, step two, where the optically pure 2-bromo acid of formula (III) may be bound to an amine functionalized bead in the presence of a coupling agent in an appropriate solvent to give a compound of formula (V):

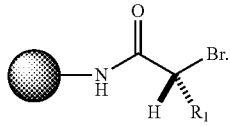

(V)

wherein $R_1$ is as defined above.

The specific amine functionalized bead is not crucial. Examples include, but are not limited to, Amidine, N-(4-Benzyloxybenzyl)hydroxylamine polymer, (Aminomethyl) polystyrene, (Aminomethyl)polystyrene, (Aminomethyl) polystyrene, (Aminomethyl)polystyrene, (Aminomethyl) polystyrene, (Aminomethyl)polystyrene, (R)-(+)-a-methylbenzylamine, 2-Chlorotrityl Knorr, 2-N-Fmoc-Amino-dibenzocyclohepta-1,4-diene, 4-[4-(1-Fmoc-aminoethyl)-2-methoxy-5-nitrophenoxy] butyramidomethyl-polystyrene, 4-Benzyloxybenzylamine, 4-Carboxybenzenesulfonamide, 4-Carboxybenzenesulfonamide, (Aminomethyl)polystyrene, (Aminomethyl)polystyrene, Bis(tert-butoxycarbonyl)thiopseudourea, Dimethylaminomethyl-polystyrene, Fmoc-3-amino-3-(2-nitrophenyl) propionic acid, N-Methyl aminomethylated polystyrene, PAL resin, Sieber amide resin, tert-Butyl N-(2-mercaptoethyl)carbamate, Triphenylchloromethane-4-carboxamide polymer, and the like.

Similarly, the size and shape of the beads are not limited. However, in some embodiments, the average particle diameter of the bead is generally in the range of about 1 to 1,000 μm, in the range of about 5 to 500 μm, or in the range of about 10 to 300 μm. The range includes the endpoints. The specific surface area of the beads can be in the range of about 0.1 to 500 $m^2/g$, 10 to 300 $m^2/g$, or 50 to 200 $m^2/g$.

In some embodiments, the amine functionalized bead may be coupled with a cleavable linker. In some embodiments, the cleavable linker is selected from, but not limited to, naturally occurring and synthetic α, β, γ, or δ amino acids. In some embodiments, the solid-phase comprises a bed having a linker, for example, methionine.

In some embodiments, the coupling agent is, for example, but not limited to, dicyclohexylcarbodiimide (DCC), diisopropylcarbodiimide (DIC), ethyl-(N',N'-dimethylamino) propylcarbodiimide hydrochloride (EDC), 3-(diethylphosphoryloxy)-1,2,3-benzotriazin-4(3H)-one (DEPBT), 4-(4,6-dimethoxy-1,3,5-triazin-2-yl)-4-methylmorpholinium chloride (DMTMM), and carbonyldiimidazole (CDI). In some embodiments, the coupling agent is diisopropylcarbodiimide (DIC).

In some embodiments, the solvent for the coupling step may be selected from, but not limited to, N,N-dimethylformamide, dimethyl sulfoxide, dioxane, and tetrahydrofuran. In some embodiments, the solvent is N,N-dimethylformamide.

In some embodiments, the method comprises a step, which can be, but is not limited to, a step three. In some embodiments, the method comprises a step where the compound of formula (V) is treated with a primary amine of formula (IV):

to produce the monomer of formula (VI):

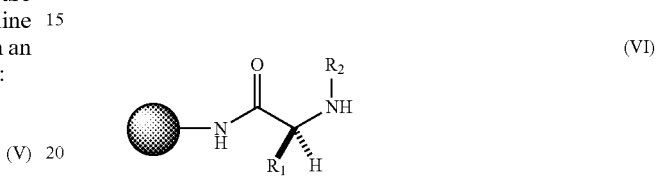

wherein $R_2$ is as defined above.

General formula (VI) is shown for the purpose of illustration purpose. It is not limited to certain chirality. For example, the chiral center at the carbon atom which $R_1$ is connected with can be in R-configuration in some embodiments, and can be in S-configuration in other embodiments.

In some embodiments, the method comprises a step, which can be repeated as necessary to achieve the desired oligomer of the peptide tertiary amide. In some embodiments, the step comprises the addition of bromide (III) followed by the addition of primary amine (IV) to monomer (VI).

In some embodiments, the oligomers of the compound of formula (VI) are released from the bead by cleaving the oligomers from the solid-phase bead by reacting the bound oligomer with a chemical, for example, cyanogen bromide.

In some embodiments, the peptide tertiary amide (PTA) comprises one or more Cα- and N-substitutions. The PTA is optically or chirally pure with a certain configuration in accordance with some embodiments. In some embodiments, the peptide tertiary amides are enantiomerically pure with either the (R) or (S) enantiomers. In some embodiments, at least one of $R_1$ and $R_2$ is an amino acid side chain. In some embodiments, the PTA comprises isotopic labeling.

In some other embodiments, 2-bromo acid of formula (III) can be in a racemic mixture comprising two chiral compounds. This can result in a mixture of PTAs having different chirality. Such a mixture can be separated to provide optically pure PTAs.

The present disclosure also provides a combinatorial library of compounds comprising a plurality of molecules of peptide tertiary amide (PTA) each having at least one unit of formula (I), as described above. In some embodiments, the plurality of molecules of PTA each has at least two, for example, three, four, five or six units, of formula (I).

III. Uses:

The peptide tertiary amides described herein can be used for various purposes. In some embodiments, the peptide tertiary amides can be used for tools for biological research and as drug leads (for example, in the treatment of cancer, infectious disease, neurological diseases, cardiac diseases and the like). The PTAs retain all of the favorable characteristics of peptoids, for example, modularity, ease of synthesis, ability to sequence compound from a single bead, predicted high cell permeability, etc. The PTAs created by, for example, the presently described method surmount a serious limitation of peptoids. The methods facilitate the ability to introduce substituents on both the α-carbon and the nitrogen, which allows the facile generation of enormous chemical diversity, while maintaining relatively low molecular mass. Moreover, these molecules will be highly cell permeable (Yu, et al., *Nature Biotech.* 2005, 23, 746-751). Yet by using 10 amino acid-derived chiral 2-bromoacids and 10 amines, for example, one can generate a library of one million different trimers quickly and easily. Since PTAs synthesized by the present disclosure are conformationally restricted, and it is generally acknowledged that conformational restriction is desirable in achieving high protein binding affinity (Lipinski, et al., *Nature* 2004, 432, 855-861 and Lipinski, *J. Pharmacol. Toxicol. Methods* 2000, 44, 235-249), the PTA libraries are a source of much higher affinity protein ligands than libraries of either peptides or peptoids.

In one embodiment, a library produced by the methods embodied herein is screened so as to identify high affinity ligands for a desired or target molecule. Examples of such target molecules include, without limitation: autoantibodies, molecules present on an immune cell associated with a disease or disorder, such as for example, autoimmunity, inflammation, transplant rejection and the like. In some embodiments, a method of identifying high affinity ligands for a molecule associated with a particular disease or disorder, such as, an antibody specific for an auto-antigen in an autoimmune disease, comprising: contacting a biological sample from a patient with a library of compounds of Formula I, identifying the ligands which bind to the desired target, e.g. antibody which is associated with that disease. In some embodiments, the target is a T cell.

In embodiments, one or more compounds of Formula I are administered in therapeutically effective doses to patients in need of therapy. Patients in need of therapy comprise those at risk of developing a certain condition, disease or disorder (e.g. due to genetic, environmental or physical attributes, such as for example, obesity). Patients in need of therapy also include those afflicted with a condition, disease or disorder. The diseases or disorders comprise, for example: autoimmune diseases, cancer, inflammatory diseases, neurological diseases or disorders, neuroinflammatory diseases or disorders, cardiovascular disease, obesity, diseases or disorders caused by infectious agents such as, for example, viruses, bacteria, fungi, prions, or parasites. For example, the compounds of Formula I may be ligands for: an autoimmune molecule, an immune cell associated with autoimmunity or inflammation (e.g. lymphocytes), a foreign antigen, cytokines etc.

In other embodiments, a method of treating a patient at risk of developing an autoimmune disease or is suffering from an autoimmune disease, comprises: screening a ligand library of compounds comprising Formula I against a particular autoantibody or immune cell molecule associated with a particular autoimmune disease or condition; identifying a high affinity ligand to a particular autoantibody or immune cell associated with a particular autoimmune disease or disorder; isolating the high affinity ligand from the library; and, treating the patient with the isolated high affinity ligand.

In one embodiment, the autoimmune disease or disorder is Pemphigus vulgaris.

In some embodiments, the invention includes methods and compositions for assessing ligand binding moieties present in autoimmune diseases. Examples of autoimmune diseases or disorders embodied herein, include without limitation: acute disseminated encephalomyelitis (ADEM), acute necrotizing hemorrhagic leukoencephalitis, Addison's disease, agammaglobulinemia, allergic asthma, allergic rhinitis, alopecia areata, amyloidosis, ankylosing spondylitis, anti-GBM/anti-TBM nephritis, antiphospholipid syndrome (APS), autoimmune aplastic anemia, autoimmune dysautonomia, autoimmune hepatitius, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, axonal & neuronal neuropathies, Balo disease, Behcet's disease, bullous pemphigoid, cardiomyopathy, Castlemen disease, celiac sprue (non-tropical), Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/henign mucosal pemphigoid, Crohn's disease, Cogan's syndrome, cold agglutinin disease, congenital heart block, coxsackie myocarditis, CREST disease, essential mixed cryoglobulinemia, demyelinating neuropathies, dermatomyositis, Devic's disease (neuromyelitis optica), discoid lupus, Dressler's syndrome, endometriosis, eosinophillic fasciitis, erythema nodosum, experimental allergic encephalomyelitis, Evan's syndrome, fibromyalgia, fibrosing alveolitis, giant cell arteritis (temporal arteritis), glomerulonephritis, Goodpasture's syndrome, Grave's disease, Guillain-Barre syndrome, Hashimoto's encephalitis, Hashimoto's thyroiditis, hemolytic anemia, Henock-Schoniein purpura, herpes gestationis, hypogammaglobulinemia, idiopathic thrombocytopenic purpura (ITP), IgA nephropathy, immunoregulatory lipoproteins, inclusion body myositis, insulin-dependent diabetes (type 1), interstitial cystitis, juvenile arthritis, juvenile diabetes, Kawasaki syndrome, Lambert-Eaton syndrome, leukocytoclastic vasculitis, lichen planus, lichen sclerosus, ligneous conjunctivitis, linear IgA disease (LAD), Lupus (SLE), Lyme disease, Meniere's disease, microscopic polyangitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars plantis (peripheral uveitis), pemphigus, peripheral neuropathy, perivenous encephalomyelitis, pernicious anemia, POEMS syndrome, polyarteritis nodosa, type I, II & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasis, Raynaud's phenomena, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Slogren's syndrome, sperm and testicular autoimmunity, stiff person syndrome, subacute bacterial endocarditis (SBE), sympathetic ophthalmia, Takayasu's arteritis, temporal arteritis/giant cell arteries, thrombocytopenic purpura (TPP), Tolosa-Hunt syndrome, transverse myelitis, ulcerative colitis, undifferentiated connective tissue disease (UCTD), uveitis, vasculitis, vesiculobullous dermatosis, vitiligo or Wegener's granulomatosis or, chronic active hepatitis, primary biliary cirrhosis, cadilated cardiomyopathy, myocarditis, autoimmune polyendocrine syndrome type I (APS-I), cystic fibrosis vasculitides, acquired hypoparathyroidism, coronary artery disease, pemphigus foliaceus, pemphigus vulgaris, Rasmussen encephalitis, autoimmune gastritis, insulin hypoglycemic syndrome (Hirata disease), Type B insulin resistance, acanthosis, systemic lupus erythematosus (SLE), pernicious anemia, treatment-resistant Lyme arthritis, polyneuropathy, demyelinating diseases, atopic dermatitis, autoimmune hypothyroidism, vitiligo, thyroid associated ophthalmopathy, autoimmune coeliac disease, ACTH deficiency, dermatomyositis, Sjogren syndrome, systemic sclerosis, progressive systemic sclerosis, morphea, primary antiphospholipid syndrome, chronic idiopathic urticaria, connective tissue syndromes, necrotizing and crescentic glomerulonephritis (NCGN), systemic vasculitis, Raynaud syndrome, chronic liver disease, visceral leishmaniasis, autoimmune C1 deficiency, membrane proliferative glomerulonephritis (MPGN), prolonged coagulation time, immunodeficiency, atherosclerosis, neuronopathy, paraneoplastic pemphigus, paraneoplastic stiff man syndrome, paraneoplastic encephalomyelitis, subacute autonomic neuropathy, cancer-associated retinopathy, paraneoplastic opsoclonus myoclonus ataxia, lower motor neuron syndrome and Lambert-Eaton myasthenic syndrome.

In other embodiments, a binding profile of one or more sample components (e.g., biomarkers) can be used to predict, diagnose, assess, or treat, any disease, known to one of skilled in the art. The terms "disease" or "condition" are commonly recognized in the art and designate the presence of signs and/or symptoms in an individual or patient that are generally recognized as abnormal. Diseases or conditions may be diagnosed and categorized based on pathological changes. Signs may include any objective evidence of a disease such as changes that are evident by physical examination of a patient or the results of diagnostic tests. Symptoms are subjective evidence of disease or a patient's condition, i.e. the patient's perception of an abnormal condition that differs from normal function, sensation, or appearance, which may include, without limitations, physical disabilities, morbidity, pain, and other changes from the normal condition experienced by an individual. Various diseases or conditions include, but are not limited to; those categorized in standard textbooks of medicine including, without limitation, textbooks of nutrition, allopathic, homeopathic, and osteopathic medicine. In certain aspects of this invention, the disease or condition is selected from the group consisting of the types of diseases listed in standard texts such as Harrison's Principles of Internal Medicine, 14$^{th}$ Edition (Fauci et al, Eds., McGraw Hill, 1997), or Robbins Pathologic Basis of Disease, 6$^{th}$ Edition (Cotran et al, Ed. W B Saunders Co., 1998), or the Diagnostic and Statistical Manual of Mental Disorders: DSM-IV, 4$^{th}$ Edition, (American Psychiatric Press, 1994), or other text books, which are incorporated herein in their entirety.

The random ligand library screening methods of the invention can use the binding characteristics to differentiate between different forms of a disease or its state, including pre-disease states or the severity of a disease state. For example, the methods may be used to determine the metastatic state of a cancer or the susceptibility to an agent or disease state. In some embodiments, the invention includes methods and compositions for assessing ligand binding moieties present in or associated with a cancer, for example, but not limited to, breast cancer, lung cancer, prostate cancer, cervical cancer, head & neck cancer, testicular cancer, ovarian cancer, skin cancer, brain cancer, pancreatic cancer, liver cancer, stomach cancer, colon cancer, rectal cancer, esophageal cancer, lymphoma, and leukemia.

In one embodiment, the invention includes methods and compositions for assessing ligand binding moieties present in infectious diseases, for example, but are not limited to, Acquired immunodeficiency syndrome (AIDS), Anthrax, Botulism, Brucellosis, Chancroid, Chlamydial infection, Cholera, Coccidioidomycosis, Cryptosporidiosis, Cyclosporiasis, Diphtheria, Ehrlichiosis, Arboviral Encephalitis, Enterohemorrhagic *Escherichia coli* (*E. coli*), Giardiasis, Gonorrhea, *Haemophilus influenzae*, Hansen's disease (leprosy), Hantavirus pulmonary syndrome, Hemolytic uremic syndrome, Hepatitis A, Hepatitis B, Hepatitis C, Human immunodeficiency virus (HIV), Legionellosis, Listeriosis, Lyme disease, Malaria, Measles, Meningococcal disease, Mumps, Pertussis (whooping cough), Plague, Paralytic Poliomyelitis (polio), Psittacosis (parrot fever), Q Fever, Rabies, Rocky Mountain spotted fever, Rubella, Congenital rubella syndrome, Salmonellosis, Severe acute respiratory syndrome (SARS), Shigellosis, Smallpox, Streptococcal disease (invasive Group A), Streptococcal toxic shock syndrome (STSS), *Streptococcus pneumoniae*, Syphilis, Tetanus, Toxic shock syndrome, Trichinosis, Tuberculosis, Tularemia, Typhoid fever, Vancomycin-Intermediate/Resistant *Staphylococcus aureus*, Varicella, Yellow fever, variant Creutzfeldt-Jakob disease (vCJD), Dengue fever, Ebola hemorrhagic fever, Echinococcosis (Alveolar Hydatid disease), Hendra virus infection, Human monkeypox, Influenza A H5N1 (avian influenza), Lassa fever, Marburg hemorrhagic fever, Nipah virus, O'nyong-nyong fever, Rift Valley fever, Venezuelan equine encephalitis, and West Nile virus.

The ligand library of the invention may be used to screen for any stage of a disease, for example, an early stage of a disease or an advanced late stage of a disease.

In yet another embodiment, the invention includes methods and compositions for assessing ligand binding moieties present in neurodegenerative diseases, for example, but are not limited to, stroke, hypovolemic shock, traumatic shock, reperfusion injury, multiple sclerosis, AIDS, associated dementia; neuron toxicity, Alzheimer's disease, head trauma, adult respiratory disease (ARDS), acute spinal cord injury, Huntington's disease, and Parkinson's Disease.

The invention comprises compositions which comprises libraries of compounds generated by the methods embodied herein and comprise compounds or ligands of Formula I.

The present invention also contemplates the use of compounds of Formula I having binding specificity to desired targets, such as an auto-immune antibody or autoreactive T cells in the context of treatments in combination with treatment of the patient with the high affinity ligand. The treatment of autoimmune diseases or any other disease as embodied herein, may be used in combination with other known treatment regimens or alone. In autoimmune disease, the body's own immune response turns upon itself. Most often, this process initiates with certain T cells becoming sensitized to the host's own antigen—a process that does not take place in healthy subjects. If these autoreactive T cells could be selectively reduced or eliminated, i.e., without affecting other T cells necessary for normal immune surveillance and activity, then autoimmune disease symptoms should at least be mitigated, if not eliminated completely. The therapies utilizing compounds embodied herein, can certainly be used to mitigate or eliminate all symptoms of the disease by removing the T-cells or other antibody producing/catalyzing cells and by preventing the destruction of the natural antigen by the autoantibody via use of the compounds embodied herein. In a preferred embodiment, the compounds are compounds of Formula I. The compounds may be conjugated to a therapeutic molecule e.g. radioisotope, toxin, pharmaceutical agent, antisense molecules and the like.

The biological samples prepared for analysis in the process of the invention include or can include a host of potential biomarkers including markers expressed on cells (non-adherent cells, including T-cells or other immune effector cells), microorganisms, proteins, peptides, lipids, polysaccharides, small molecules, organic molecules, inorganic molecules, biological molecules and including any detectable or readable moiety in such complex milieu. In a preferred embodiment, such markers are antibodies and, in particular, are antibodies generated as a result of a disease or condition. In a preferred embodiment, body fluids such as serum, plasma, saliva or other fluids or samples derived from a patient or animal or organism are the source of such markers. Each sample or tissue or biologically derived, or environmentally derived or obtained sample can be conditioned, or treated or diluted, or otherwise handled in order to expose the sample to either the initial screening or any subsequent screening using putative hits or ligands which have affinity for such biomarkers. The samples can be diluted to provide or permit sufficient distinction between background levels or noise and signals associated with the binding of a ligand to a ligand binding moiety.

The time and/or conditions necessary to expose the library of compounds or ligands to such samples depend upon the particular sample and other factors. In almost all cases, washing or eluting steps and other conditioning means are utilized following exposure of the biological fluid to the large ligand library and/or ligands or kits derived from such library. Aqueous solutions are utilized including buffered solutions such as HEPES buffer, Iris buffer or phosphate buffered saline. Support systems may also be treated with energy absorbing materials to facilitate desorption or ionization of a "complex" from a support surface. Chemical means are also utilized to decouple or remove ligand-ligand binding moiety complexes from supports.

Detection methods for detecting ligand-ligand binding moiety complexes on a support include photometric and non-photometric means. Such methods include ensuring that the process includes a method to detect and measure absorbance, fluorescence, refractive index, polarization or light, scattering. These include direct and/or indirect means to measure such parameters. Methods involving fluorescence include fluorescent tagging in immunological methods such as ELISA or sandwich assay. Methods involving refractive index include surface plasmon resonance (SPR), grating coupled methods (e.g. sensors uniform grating couplers, wavelength-interrogated optical sensors (WIOS) and chirped grating couplers), resonant mirror and interferometric techniques. Methods involving polarization include ellipsometry. Light scattering methods may also be used. Other means for tagging and/or separating and/or detecting can also include magnetic means. Magnetic resonance imaging, gas phase ion spectrometry, MRI may all be used.

Analysis of the data generated typically involves quantification of a signal due to the detected biomarker versus a control or reference. The data can be analyzed by any suitable means. Computers and computer programs may be utilized to generate and analyze the data. Beads and/or other supports may be computer coded or coded for identification purposes. Data analysis includes analysis of signal strength under the particular conditions of the assay or detection method, ligands, ligand binding moieties or reference moieties and/or secondary detection moieties may be labeled or radio-labeled or tagged with a detectable moiety. One of ordinary skill in the art can assess the difference and/or distinction between biological fluid samples that have disease associated biomarkers versus those control or healthy patient, samples that do not contain such markers. One of ordinary skill in the art can also determine, pursuant to the methods described herein, the presence of false positives or other hits that are or may be found in control samples to account for and/or remove such "hits" and one of ordinary skill in the art, pursuant to the methods described herein, can continue the process of determining or finding disease associated biomarkers in patient samples having tray disease or condition. The "detection" of such hits, in all cases, is accomplished by means for detecting the binding of a ligand-binding moiety such as a disease associated biomarker or other markers to ligands in a ligand library such as those described herein.

Biomarkers associated with the diseases and/or conditions recited herein will vary depending upon the particular stage of the disease and/or condition of the particular patient or animal or other organism assessed. The ligands, which are the putative hits and the compounds recited herein, are expected to, in most cases, mimic the natural antigen that initiates the immune response and/or formation of antibodies or immune cells in the first instance. The present invention and screening process claimed and recited herein does not require knowledge of either the particular antigen or the antibody generated in response to the antigen. The ligands, however, may be useful in their own right as vaccines or drug candidates in addition to being useful in the screens and diagnostic methods recited herein. The present invention thus includes compounds and pharmaceutical compositions.

In embodiments, biological samples are screened for high affinity ligands specific for biomarkers or markers expressed by immune system memory cells such as for example: mTOR, mTOR complex, mTORC1, mTORC complex, raptor, Blimp-1, T-box transcription factor (TBX21; T-bet), Glycogen synthase kinase 3 (GSK3), B-cell CLL/lymphoma (Bcl-6), eomesodermin (Eomes), testosterone conversion factor (TCF-1), wnt, β-catenin, tumor necrosis factor (TNF) receptor-associated factor 6 (TRAF6), AMP-activated protein kinase (AMPK), TRAF6/AMPK, 4-1BB, OX40, CD27, cytokines, IL-2, IL-12, IL-15, IL-21, interferons (IFN), CD4, intracellular mediators of $CD8^+$ T cell differentiation, or combinations thereof.

In another embodiment, the high affinity ligands are specific for $CD8^+$ T cell markers comprising: CD137 (4-1BB), IFN-γ, TNF-α, CD11a/CD18 (LFA-1), CD2, CD49d/CD29 (VLA-4), CD8 or combinations thereof. In other embodiments, the high affinity ligands are specific for one or more immune cell molecules comprising: 4-1BB (CD137), B7-1/2, 4-1BBL, OX40L, CD40, LIGHT, OX40, CD2, CD3, CD4, CD8a, CD11a, CD11b, CD11c, CD19, CD20, CD25 (IL-2Rα), CD26, CD27, CD28, CD40, CD44, CD54, CD56, CD62L (L-Selectin), CD69 (VEA), CD70, CD80 (B7.1), CD83, CD86 (B7.2), CD95 (Fas), CD134 (OX-40), CD137, CD137L, (Herpes Virus Entry Mediator (HVEM), TNFRSF14, ATAR, LIGHTR, TR2), CD150 (SLAM), CD152 (CTLA-4), CD154, (CD40L), CD178 (FasL), CD209 (DC-SIGN), CD 270, CD277, AITR, AITRL, B7-H3, B7-H4, BTLA, HLA-ABC, HLA-DR, ICOS, ICOSL (B7RP-1), NKG2D, PD-1 (CD279), PD-L1 (B7-H1), PD-L2 (B7-DC), TCR-α, TCR-β, TCR-γ, TCR-δ, ZAP-70, lymphotoxin receptor (LTβ), NK1.1, HLA-ABC, HLA-DR, T Cell receptor αβ (TCRαβ), T Cell receptor γδ (TCRγδ), T cell receptor ζ (TCRζ), TGFβRII, TNF receptor, Cd11c, CD1-339, B7, Foxp3, mannose receptor, or DEC205, variants, mutants, species variants, ligands, alleles and fragments thereof.

In embodiments, immune cells or cells of the immune system comprise T cells (T lymphocytes), B cells (B lymphocytes), antigen presenting cells, dendritic cells, monocytes, macrophages, myeloid suppressor cells, natural killer (NK) cells, NK T cells, suppressor cells, $CD4^+$ T cells, T regulatory cells (Tregs), cytotoxic T lymphocytes (CTLs), CTL lines, CTL clones, CTLs from tumor, inflammatory, or other infiltrates and subsets thereof. Any one or more of these cells can be targeted to identify high affinity ligands.

In other embodiments, a method of treating a disease in a patient, the method comprising: obtaining a biological sample from the patient; screening the sample with a library comprising at least one ligand to determine a ligand binding profile; administering a drug to the patient, based on the results of the ligand binding profile in the patient, wherein the at least one ligand has an affinity to one or more antibodies associated with the disease.

In another embodiment, a method of monitoring a treatment by a drug in a subject, the method comprising: obtaining a biological sample from the subject; screening a ligand library against the subject; identifying binding characteristics of one or more markers in the sample with one or more ligands in the library; determining whether the one or more markers are associated with a response to a drug for treating the disease; administering the drug to the subject, based on the determination of association between the one or more markers to the response, thereby monitoring the treatment by the drug in the subject.

In another embodiment, a method of detecting a risk of adverse reaction to a drug in a subject, the method comprising: obtaining a biological sample from the subject; screening a ligand library against the sample; identifying binding characteristics of one or more markers in the sample with one or more ligands in the library; and determining whether the one or more markers are associated with the risk, thereby detecting the risk of adverse reaction to the drug in the subject.

The large ligand libraries embodied herein can be used directly in biological fluid, under the appropriate experimental conditions, to screen for biomarkers and without the need to use fewer support members (e.g. about 100,000 or less) or requirement to transfer such peptide tertiary amides (PTAs) having diverse N-substitution (ligands) to a microarray before screening the biological fluid. In addition, the ligand libraries may also be used to screen for cell based receptors that specifically relate to a particular cell surface marker. The present invention, permits the inclusion of greater numbers of beads/resins and thus larger libraries in either the ligand binding agent screen or the cell receptor screen to directly screen the complex biological samples.

With respect to microarray systems, virtually any molecule or compound may be used to build a random bead or resin based library.

IV. Kits

Any of the compositions described herein may be comprised in a kit. In a non-limiting example, conformationally restrained peptide tertiary amides or compounds of Formula I, Formula I arrays, and related support(s), buffers, linkers, and reagents are provided in a kit. The kit may further comprise reagents for processing a sample and/or sample components. The kit may also comprise reagents that may be used to label various components of an array or sample, with for example, radio isotopes or fluorophors.

Kits for implementing methods of the invention described herein are specifically contemplated. In some embodiments, there are kits for synthesis, processing, and detection of combinatorial libraries of compounds of Formula I.

The components of the kits may be packaged either in aqueous media or in lyophilized form. The container means of the kits will generally include at least one vial, test tube, plate, flask, bottle, array substrate, syringe or other container means, into which a component may be placed, and preferably, suitably attached. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing binding elements or reagents for synthesizing such, and any other reagent containers in close confinement for commercial sale. Such containers may include injection or blow molded plastic containers into which the desired vials are retained.

When components of the kit are provided in one and/or more liquid solutions, the liquid solution is typically an aqueous solution that is sterile and proteinase free. In some cases proteinatious compositions may be lyophilized to prevent degradation and/or the kit or components thereof may be stored at a low temperature (i.e., less than about 4° C.). When reagents and/or components are provided as a dry powder and/or tablets, the powder can be reconstituted by the addition of a suitable solvent. It is envisioned that the solvent may also be provided in another container means.

V. Definitions:

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, up to 1% of a given value. Alternatively, particularly with respect to biological systems or processes, the term can mean within an order of magnitude, such as within 5-fold or within 2-fold, of a value. Where particular values are described in the application and claims, unless otherwise stated the term "about" meaning within an acceptable error range for the particular value should be assumed.

The terms, "compound" and "compounds" or "ligands" as used herein refers to a compound encompassed by the generic formulae disclosed herein, any subgenus of those generic formulae, and any forms of the compounds within the generic and sub-generic formulae. Unless specified otherwise, the term further includes the racemates, stereoisomers, and tautomers of the compound or compounds.

The term "combinatorial library" as used herein refers to a set of compounds or materials prepared by combinatorial chemistry. In some embodiments, a library optionally includes a collection of pools or sub-libraries. A "sub-library" means a sub-set of compounds or materials, e.g., a collection of materials or compounds obtained from solid phase synthesis units, e.g., within a particular container or vessel in the methods described herein.

The term "building block" as used herein refers to one of a number of interchangeable reagents which are optionally used in combinatorial library synthesis, at least part of the structure of which becomes incorporated into an intermediate or final product. Building blocks or components may include a set of reagents that introduces diversity into library products and/or one that results in an identical conversion for each member of the library.

The term "linker" as used herein refers to a bi-functional chemical moiety attaching a compound to, e.g., a solid support which can be cleaved to release materials or compounds from the support. Choice of linker allows cleavage to be performed under appropriate conditions compatible with the stability of the compound and assay method. Additional description of linker molecules is provided in, e.g., Backes et al., *Curr. Opin. Chem. Biol.* 1997, 1, 86-93, Backes et al., *J. Amer. Chem. Soc.* 1996, 118, 3055-3056, Backes et al., *J. Amer. Chem. Soc.* 1994, 116, 11171-11172, Hoffmann et al., *Tetrahedron Lett.* 1994, 35, 7763-7766, Kocis et al., *Tetrahedron Lett.* 1993, 34, 7251-7252, and Plunkett et al., *J. Org. Chem.* 1995, 60, 6006-6007.

The term "cleavage" as used herein refers to a process of releasing a material or compound from a solid support, e.g., to permit analysis of the compound by solution-phase methods.

The term "solid phase synthesis" as used herein refers to a method in which molecules are bound on a bead and synthesized step-by-step in a reaction solution.

The term "semi-solid phase synthesis" as used herein refers to a method in which the molecules are admixed with resins, such as for example, epoxy-resins or any granular material, with preference being given in particular to beads. The latter are particularly preferably magnetic beads. Such materials are commercially available, for example epoxy-modified magnetic beads (DYNAL®).

The term "monomer" as used herein refers to a single molecular unit that may chemically bond to other monomers to form polymers or oligomers.

The term "oligomer" as used herein refers to a molecule that is made up of a finite number of monomers.

The term "target molecule" includes any macromolecule, including protein, carbohydrate, enzyme, polysaccharide, glycoprotein, receptor, antigen, antibody, growth factor; or it may be any small organic molecule including a hormone, substrate, metabolite, cofactor, inhibitor, drug, dye, nutrient, pesticide, peptide; or it may be an inorganic molecule including a metal, metal ion, metal oxide, and metal complex; it may also be an entire organism including a bacterium, virus, and single-cell eukaryote such as a protozoon.

The term "alkyl" as used herein refers to a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Alkyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, or as known to those skilled in the art, for example, as taught in T. W. Greene and P. G. M. Wuts, "Protective Groups in Organic Synthesis," $3^{rd}$ ed., John Wiley & Sons, 1999, hereby incorporated by reference.

The term "alkenyl" as used herein refers to an unsaturated straight, branched, or cyclic, primary, secondary, or tertiary hydrocarbon of typically $C_1$ to $C_{10}$, that has one or more double bonds. The term includes both substituted and unsubstituted alkenyl groups. Alkenyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate.

The term "alkynyl" as used herein refers to an unsaturated straight, branched, or cyclic, primary, secondary, or tertiary hydrocarbon of typically $C_1$ to $C_{10}$, that has one or more triple bonds. The term includes both substituted and unsubstituted alkynyl groups. Alkynyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate.

The terms "alkylamino" or "arylamino" as used herein refer to an amino group that has one or two alkyl or aryl substituents, respectively.

The term "aryl" as used herein refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate.

The term "alkaryl" as used herein refers to an alkyl group with an aryl substituent.

The term "acyl" as used herein refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen (F, Cl, Br, I), $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group.

As used herein, the term "alkoxy" refers to an optionally substituted straight or branched chain alkyl-O— group wherein alkyl is as previously defined. For example, $C_{1-10}$ alkoxy means a straight or branched alkoxy containing at least 1, and at most 10, carbon atoms. Examples of "alkoxy" as used herein include, but are not limited to, methoxy, ethoxy, propoxy, prop-2-oxy, butoxy, but-2-oxy, 2-methyl-prop-1-oxy, 2-methylprop-2-oxy, pentoxy and hexyloxy. A $C_{1-4}$ alkoxy group is preferred, for example methoxy, ethoxy, propoxy, prop-2-oxy, butoxy, but-2-oxy or 2-methylprop-2-oxy. As used herein, the term "aryloxy" refers to an optionally substituted aryl-O-group wherein aryl is as previously defined. Exemplary aryloxy groups include, but are not limited to, phenoxy (phenyl-O—).

As used herein, the term "heteroaryl" refers to an optionally substituted aryl ring system wherein, in at least one of the rings, one or more of the carbon atom ring members is independently replaced by a heteroatom group selected from the group consisting of S, O, N, and NH, or NR wherein aryl is as previously defined and R is an optional substituent as defined herein. Heteroaryl groups having a total of from about 5 to about 14 carbon atom ring members and heteroatom ring members (and all combinations and subcombinations of ranges and specific numbers of carbon and heteroatom ring members) are preferred. Heteroaryl groups having a total of from about 5 to about 10 carbon atom ring members and heteroatom ring members (and all combinations and subcombinations of ranges and specific numbers of carbon and heteroatom ring members) are more preferred. Exemplary heteroaryl groups include, but are not limited to, pyrryl, furyl, pyridyl, pyridine-N-oxide, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be attached to the rest of the molecule via a carbon or a heteroatom.

As used herein, the term "heteroarylalkyl" refers to an optionally substituted ring system comprising an alkyl radical bearing a heteroaryl substituent, each as defined above, having at least 6 carbon atoms, for example, from about 6 to about 25 carbon atoms (and all combinations and subcombinations of ranges and specific numbers of carbon atoms therein).

As used herein, the term "heterocycloalkyl," "heterocyclic ring" and "heterocyclyl" each refer to an optionally substituted ring system composed of a cycloalkyl radical wherein, in at least one of the rings, one or more of the carbon atom ring members is independently replaced by a heteroatom group selected from the group consisting of O, S, N, and NH, or NR wherein cycloalkyl is as previously defined and R is an optional substituent as defined herein. Heterocycloalkyl ring systems having a total of from about 3 to about 14 carbon atom ring members and heteroatom ring members (and all combinations and subcombinations of ranges and specific numbers of carbon and heteroatom ring members) are preferred, more preferably from about 3 to about 10 ring atom members.

The term "amino acid" as used herein refers to naturally occurring and synthetic α, β, γ, and δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of α, β, γ, and δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The terms "enantiomerically pure" or "optically pure" as used herein refer to a compound that comprises at least approximately 90%, and preferably approximately 97%, 98%, 99% or 100% of a single enantiomer of that compound.

As used herein, a "pharmaceutical salt" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

As used herein, a "pharmaceutically acceptable" component/carrier etc is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

"Biological samples" include solid and body fluid samples. Preferably, the sample is obtained from heart. However, the biological samples used in the present invention can include cells, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils and thymus. Examples of "body fluid samples" include, but are not limited to, blood, serum, semen, prostate fluid, seminal fluid, urine, saliva, sputum, mucus, bone marrow, lymph, and tears.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

An "auto-antibody" is an antibody specific for self-antigens. Examples include antibodies generated during an autoimmune disease, inflammation or the like.

While the present invention has been described in conjunction with specific embodiments set forth above, many alternatives, modifications and variations thereof will be apparent to those of ordinary skill in the art. All such alternatives, modifications and variations are intended to fall within the spirit and scope of the present invention.

EXAMPLES

While various embodiments of the present invention have been described above, it should be understood that they have been presented by way of example only, and not limitation. The following non-limiting examples are illustrative of the invention.

Example 1

General Procedure for the Conversion of Natural/Unnatural Amino Acids to α-Bromo Substituted Amino Acids FIG. 2A shows general preparation of α-bromo substituted amino acids as PTA building blocks. In the case of L-alanine to (S)-2-bromopropanoic acid, L-alanine (17.8 g, 0.2 mol) was dissolved in 200 ml of a 16% solution of HBr in water and cooled to −20° C. in a dry ice/ethylene glycol bath. NaNO$_2$ (27.6 g, 0.4 mol) was dissolved in minimum amount of water and loaded into a pressure-equalizing dropping funnel. The whole system was then flushed with argon and kept under argon at −20° C. NaNO$_2$ was slowly added dropwise into the solution of L-alanine over a period of 2 hours with vigorous stirring and the resulting solution was allowed to warm to room temperature. After 2 hours, the solution was put under high vacuum for 30 min and then extracted by ethyl ether 3 times. The organic phase was then combined and dried over anhydrous Na$_2$SO$_4$. After evaporation of ethyl ether, desired product was obtained as a pale yellow oil in high purity (>95% according to $^1$H NMR). It was further purified by reduced pressure distillation at 120° C. under high vacuum to obtain the pure compound as a colorless oil. Scheme 1 below shows preparation of chirally pure 2-bromo acids with good yield. Using a coupling agent such as diisopropylcarbodiimide (DIC), 2-bromo acids can be further used to synthesize chirally pure peptoid. For example, FIG. 3 shows crude $^1$H NMR of two diastereomers synthesized by peptoid sub-monomer synthesis using diisopropylcarbodiimide (DIC).

Scheme 1. General Preparation of Chirally Pure 2-bromo Acid

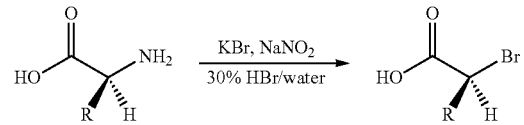

R=side chains from amino acids such as: Ala, Phe, Val, Leu, Ile, Ser, Thr, Glu, Asp etc. 64%~87% overall yield

| Starting Material | Yield |
|---|---|
| L/D-alanine | 82% |
| L/D-phenylalanine | 87% |
| L/D-serine | 64% |
| L/D-leucine* | 79% |
| L/D-isoleucine* | 81% |
| L/D-threonine | 73% |
| L/D-valine* | 82% |
| L/D-glutamic acid** | 70% |
| L/D-aspartic acid | 69% |

*Purified by recrystallization in dichloromethane/methanol.

**(R)-2-bromopentanedioic acid, shown below and derived from D-glutamic acid, has not been found in the current CAS registry.

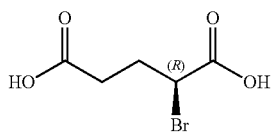

Example 2

General Procedure for Coupling in Solid-phase Synthesis of PTAs

FIG. 2B shows general procedures for making PTAs through solid-phase sub-monomer synthesis. α-bromo substituted PTA building blocks can react with beads having amine group in the presence of a coupling agent such as DIC or DMTMM. For example, a typical procedure for the 4-(4,6-dimethoxy-1,3,5-triazine-2-yl)-4-methyl-morpholinium chloride (DMTMM) activated coupling is as follows. DMTMM (0.5 g, 1.8 mmol) was added to a solution of (R)-bromopropionic acid (228 mg, 1.5 mmol) in dry THF. The solution was then allowed to shake on a shaker for 5 min and then added to the beads that end with a secondary amine. The beads with the solution were allowed to shake on the shaker for 12 hours with continuous check with a chloranil test until the coupling was complete.

In the case of serine/threonine derived PTA building block which contain hydroxyl group, DMTMM in THF was used as coupling reagent and the reaction was allowed for longer time. In some embodiments, DIC is a preferred coupling agent.

Example 3

General Procedure for Solid-phase Synthesis of PTAs

As shown in FIG. 2B, PTAs can be synthesized through repeated steps of coupling and amination. For example, Knorr amide beads were deprotected by 20% piperidine/DMF solution and the first peptoid monomer was prepared via peptoid synthesis. (R) or (S) bromopropionic acid, respectively, were activated by DIC in a 1:1 ratio in DMF and then applied to the beads. After acylation, the amine replacement was conducted by mixing a 2M solution of allylamine in DMF with the washed beads from the last step. The beads and the amine solution were shaken in a shaker at 50° C. until completion. The acylation through the coupling reaction and amination steps were then repeated. When a PTA reaches to a certain length, the PTA can be cleaved from the beads.

To create PTAs via solid-phase sub-monomer synthesis, an optically pure 2-halo carboxylic acid was used. Both (R)- and (S)-2-methylethanoic acid, which are commercially available, can be used. One question to address was whether each of the two steps of the sub-monomer synthesis would proceed without significant loss of stereochemical purity. To investigate this, compounds 1 and 2 (as shown in FIG. 4A) were synthesized, which differ only in the stereochemistry at the second chiral center and these compounds were analyzed by HPLC. The chromatograms suggested a high yield since only a single predominant peak was observed that was shown by mass spectrometry to correspond to the product (FIG. 4A).

Moreover, these diasteromers displayed significantly different Rf values under these conditions. There was no evidence for significant racemization during the synthesis, which would have produced compound 1 during the synthesis of compound 2 and vice versa. To further test the stereochemical fidelity of this reaction sequence, dimers 3 and 4 (as shown in FIG. 4B) were synthesized, which employed different amines than were used to construct 1 and 2. In this case, the diastereomers were not resolvable by HPLC, but the $^1$H NMR spectra of these compounds provided strong evidence that little or no racemization occurred during synthesis. For example, compound 1 showed only two quartets representing the protons at the two chiral centers at approximately 5.05 and 4.83 ppm, respectively (FIG. 4B).

The corresponding resonances in compound 2 were observed at different chemical shifts. No trace of these resonances was observed in the spectrum of 3. It was concluded from these data that no significant loss of stereochemical purity occurred during the synthesis of these compounds and that the sub-monomer route employed for peptoid synthesis also provides ready access to PTAs.

Example 4

Isotopic Labeling

PTAs can be identified structurally, and therefore, structural identification can be relevant. For peptoid library, tandem mass spectrometry was generally used to obtain structural information from the "hit" identified from the on bead screening. For PTAs, when both R and S isomers of the same PTA building block are used in one library, they will be indifferentiable in the mass spectrometry, thus stereochemical information cannot be obtained.

In order to be able to incorporate both the R and S enantiomer into the PTA library while keeping the library sequencable by mass spectrometry, it was decided to make isotopic labeled PTA building blocks. Transaminase (EC 2.6.1.2) has been used to transform L-alanine into D5-L-alanine. By using the same method CD5-L-alanine could be transformed into D4-bromopropionic acid.

D4-(R)-bromopropionic acid was synthesized as follows (FIG. 4C). L-alanine together with alpha-ketoglutarate as co-substrate was incubated with transaminase in pD=8.5, D$_2$O at 37° C. overnight with mild shaking. After purification more than 90% of the L-alanine was transformed into tetra-deteuro L-alanine. The yield was determined by both optical rotation and $^1$H NMR. The procedure was repeated 3 times, >98% pure deuterium labeled L-alanine was obtained. This procedure has several advantages, including but not limited to, that it can be performed at a relatively large scale (>30 g) since L-alanine, D$_2$O and transaminase are cheap and easily accessible.

For example, the following experimental procedures were used for isotopic labeling of alanine. L-alanine (300 mg, 3.36 mmol) was dissolved in 10 ml of D$_2$O, α-ketoglutarate (10 mg, 0.068 mmol) was then added as co-substrate, the whole system was then warmed up to 37° C. and adjusted pD to 8.5~8.7 with NaOD. Alanine transaminase (0.1 mg, EC 2.6.1.2 from pig heart, Roche Diagnostics, Indianapolis, Ind.) was added, and incubated at 37° C. overnight with mild shaking 90% of D2O was recovered by distillation and L-alanine-d5 was obtained by lyophilization.

However, alanine transaminase did not react sufficiently with amino acids other than alanine and glutamic acid. Some of the other amino acid can be partially isotopic labeled with different transaminases such as isoleucine transaminase. With the (S)-bromopropionic acid and D-4-(R)-bromopropionic acid, a small library with both enantiomers was synthesized.

(S)-bromopropionic acid was used together with its deuterated enantiomer to construct a testing trimer PTA library with 15 amines. The theoretical diversity of the library was 15^3*2^3=27,000. The 15 amines were chosen carefully in a way that any combination of any amine and PTA building block could be differentiated on the mass spectrum. In order to facilitate the sequencing afterwards, a short peptoid as linker was used in front of the trimer PTA shown in FIG. 5.

Figure 5:
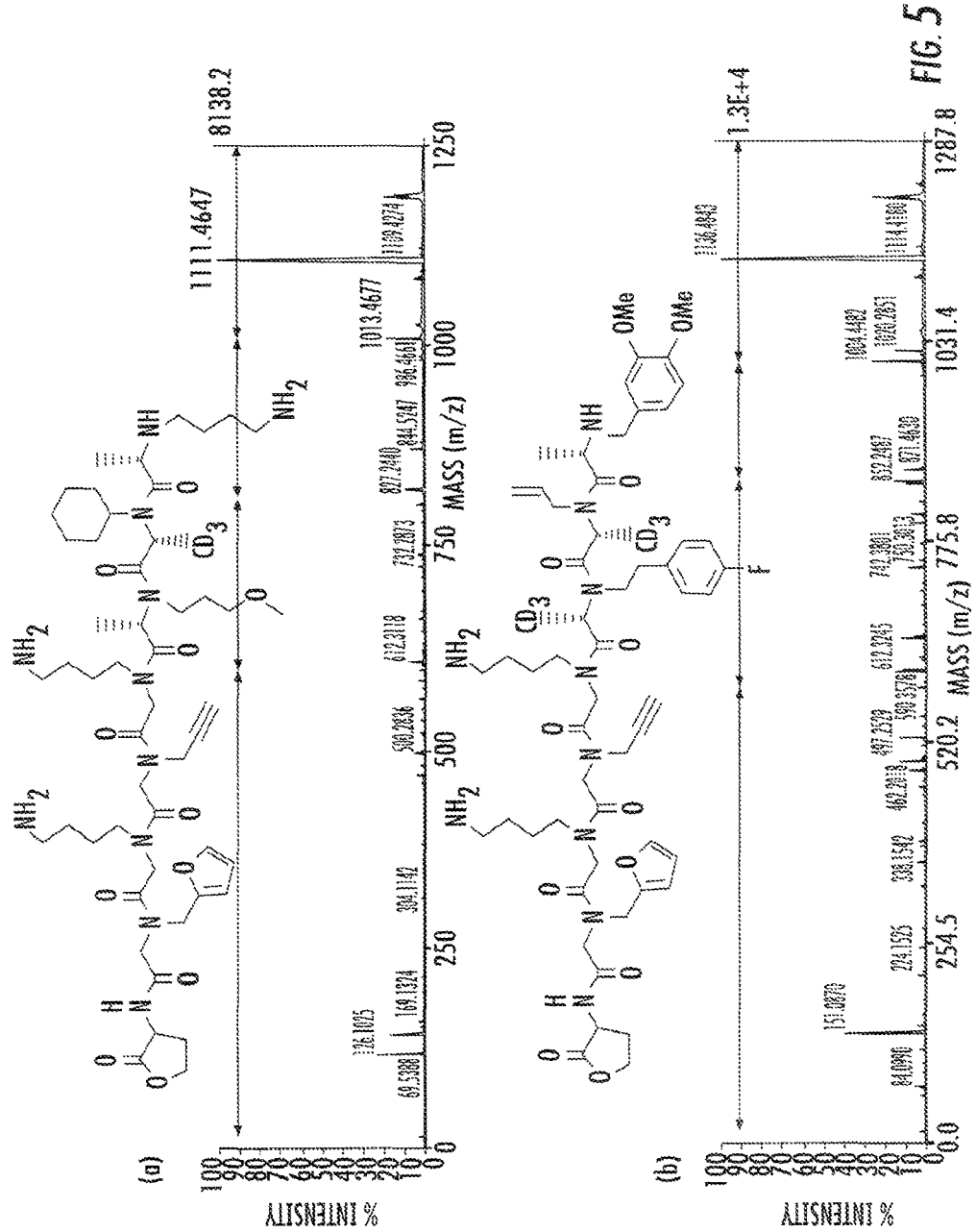
FIG. 5 shows the results from a mass spectrum of two randomly picked PTAs from the library contain both (R) and (S) propionic acid in some embodiments.

The synthesis was conducted on Tentagel® beads. Methionine was coupled by peptide coupling condition as cleavable linker. The linker peptoid was synthesized by peptoid synthesis. Then the library was split in two, one half was treated with DIC and (S)-bromopropionic acid and another half was treated with DIC and the D4-(R)-bromopropionic acid. The library was then mixed together and then split in 15 equal parts, 15 amines were then added just as peptoid synthesis and were allowed to react till completion. The same procedures were then repeated three times in order to form the trimer. The bromopropionic acid coupling step was monitored by a chloranil test and the amine substitution was monitored by silver acetate test. After the final step, the whole library was washed thoroughly and 20 beads were picked randomly. PTAs were cleaved from these 20 beads using CNBr, and sent for mass spectrometry. Seventeen out of twenty beads were sequenced (85% percent). All the 15 amines and two PTA building block used were found in the sequences. Two typical mass spectra are shown in FIG. 5.

Example 5

Engineer Strepscaffold Protein

Streptavidin, a biotin-binding protein, was used as an initial model to develop a crystallization platform for peptoid/PTA. Two independent sets of mutations (F29L, S52G, R53S, to increase the mechanostability) and (E44I, S45G, V47R, to improve the Strep-tag II binding affinity) were introduced to the original *Streptomyces avidinii* streptavidin sequence. The gene was codon optimized for *E. coli* expression and synthesized from IDT DNA (Coralville, Iowa). It was then subcloned to a homemade pHisTEV vector to generate a construct with a N-terminal His6-tag followed by a TEV protease cleavage site. Ser112 at the edge of the biotin-binding pocket was mutated to Cys to generate strepscaffold by site-directed mutagenesis method (Stratagene, Santa Clara, Calif.).

Example 6

Protein Purification, Ligand Conjugation and Crystallization

The 127 aa full length strepscaffold within pHisTEV vector was overexpressed in *Escherichia coli* BL21(DE3) cells. The temperature of the bacterial culture was dropped to 16° C. 2 h before induction and was then induced with 0.2 mM IPTG for 20 h at 16° C. The cell pellet (from 4-8 liter) was lysed in a lysis buffer (500 mM NaCl, 20 mM Tris-HCl pH 8.0, 15 mM imidazole), loaded onto a Ni-HiTrap column and washed with washing buffer (500 mM NaCl, 20 mM Tris-HCl pH 8.0, 30 mM imidazole). Protein was eluted with elution buffer (500 mM NaCl, 20 mM Tris-HCl pH 8.0, 250 mM imidazole). The protein was cleaved by adding 1:100 purified TEV protease and the cleaved N-terminal His6-tag was removed by passing through a Supperdex 200 column (GE healthcare). The purified strepscaffold protein was concentrated and stored in the final buffer (20 mM Tris-HCl pH 8.0, 150 mM NaCl).

Ligation was carried out by mixing 50 µM strepscaffold with 450 µM peptoid/PTA or DMSO as control. The ligation reaction was monitored by SDS-PAGE gel under unreduced condition. The final optimized ligation time took 36 hr at room temperature with about 80-100% strepscaffold conjugated with peptoid/PTA. The reaction was stopped by spinning out the free peptoid/PTA using 10 KDa molecular weight cutoff membrane and final protein was concentrated to 4 mg/ml before crystallization.

Crystallization was performed by the sitting-drop vapor-diffusion method at 18° C. High quality crystals of strepscaffold conjugated both peptoid and PTA were obtained in multiple conditions. These crystals were transferred to cryoprotectant solutions (with extra 20% glycerol) and flash frozen in liquid nitrogen prior to data collection.

X-ray diffraction data were collected at beamline LS-CAT station 21-ID-G, F at the Advanced Photo Source (Argonne National Laboratory). Data were processed and scaled using HKL2000. The streptavidin structure (PDB 1KL5) was used as a search model for molecular replacement using Molrep. Iterative model building and refinement were performed with Coot and PHENIX suite. Each structure has only one strepscaffold protein monomer per asymmetric unit that forms two tetramers in one cell unit. Density of conjugated peptoid/PTA was seen in the initial density and added to the model after R-factor dropped to 0.30 based on unbiased omit density map. The final six structures were refined to 1.69-2.20 Å with all residues in good geometry.

Example 7

A Combinatorial Library of PTA Tetramers Via Solid-phase Sub-monomer Synthesis

A combinatorial library of PTA tetramers using (S)-2-bromopropanoic acid and 15 different amines was created. The synthesis was carried out using a sub-monomer protocol on 160 µm TENTAGEL® beads that had first been modified with the methionine-containing linker shown in Scheme 2.

Scheme 2. TENTAGEL® Beads Modified with Methionine Linker

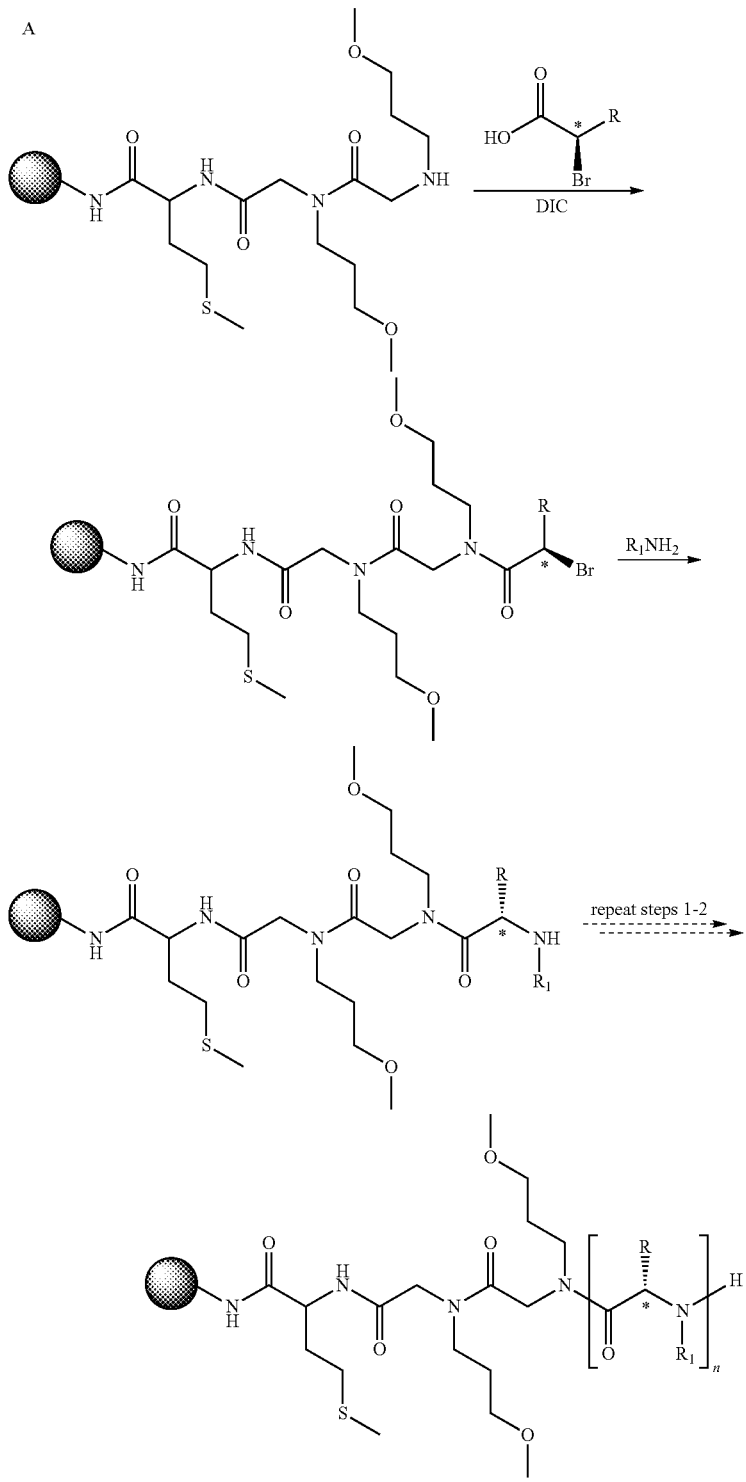

Several beads were picked randomly from the library and the immobilized molecules were released into solution by cleavage of the methionine-containing linker with cyanogen bromide. Strong molecular ion peaks were observed in the MALDI-TOF mass spectrum that corresponded to expected members of the library. The spectra looked clean in that they lacked other strong ions indicative of significant impurities. This indicates that the library is of a high-quality. The sequence of the molecules could be determined by tandem MALDI-TOF-TOF mass spectrometry.

To probe the structural properties of these compounds, initially the focus was on determining if PTAs indeed exhibited the expected strong bias in favor of the trans amide bond geometry. Conversion between amide bond isomers is slow on the NMR time scale. Therefore, the fact that only a single quartet is observed for the C5 methine proton of compound 4 in the $^1$H NMR shows that one of the two amide bond isomers predominates in solution. To determine if this is the cis- or trans-amide bond isomer, an NOE experiment was done in which the C5 methine proton resonance was saturated. A strong NOE between the N-terminal methine proton and the N-methyl protons (as well as the benzylic protons) was observed. This would be expected for the trans-amide bond isomer, but not the cis-amide bond isomer. Thus, it was concluded that the central amide bond in PTA 4 exists predominantly in the trans conformation.

In summary, it was demonstrated that PTA building blocks can be synthesized from natural amino acids with high yield and optical purity. These PTA building blocks are compatible with a sub-monomer synthesis method and, therefore, can be used in the synthesis of high-quality OBOC libraries. The absolute stereochemistry at Cα can be determined using deuterium labeling of one of the enantiomers. Finally, PTAs have far greater conformational constraints than peptoids or peptides and thus can serve as a superior scaffold for the development of high affinity protein ligands.

In the present disclosure, an effective synthetic route was identified to synthesize libraries of N-substituted oligoalanines that employs sub-monomer chemistry, which can also be used for peptoid synthesis, when bromoacetic acid other than optically pure 2-bromopropanoic acid is used. Several pieces of evidence demonstrate that both the acylation and amination steps used to create each monomeric unit of the molecule proceed with high stereochemical fidelity. As anticipated from simple modeling, the amide bond in these molecules strongly favors the trans geometry, unlike simple peptides, which generally exist as a mixture of amide bond isomers. While the structural studies have not yet provided direct evidence for significant preferences relative to conformations about the carbonyl-Cα and Cα-nitrogen bonds, these are thought to be so based on the conformation of poly-N-methylalanine and well-accepted principles of acyclic conformational analysis. Thus, it is believed that N-substituted alanines and, more generally, PTAs will be far less flexible molecules than simple peptides. This will result in the discovery of higher affinity primary hits from library screening experiments and an easier route to hit optimization. Moreover, PTAs retain all of the favorable features of peptoids, including ease of library synthesis, hit characterization and favorable physical properties. While this example employed only 2-bromopropanoic acid as a building block, it is possible to synthesize PTAs with a variety of substituents at the Cα position if the appropriate optically pure 2-bromocarboxylic acids are available.

Example 8

N-methyl-(S)-alanine Oligomers

Figure 6:
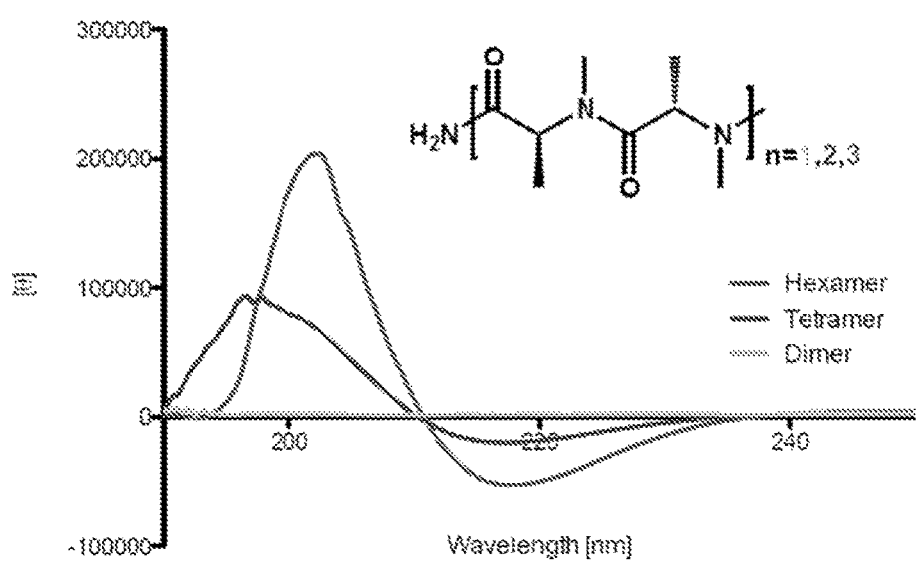
FIG. 6 shows CD spectrum of the N-methyl-alanine dimer, tetramer and hexamer synthesized via the sub-monomer route in accordance with some embodiments.

To determine if oligomers prepared via the sub-monomer route indeed display the anticipated conformational constraints, we constructed N-methyl-(S)-alanine oligomers of various lengths via the sub-monomer route on Rink amide resin. As shown in FIG. 6, an increased circular dichroism signal was observed as the length of the oligomer increased from a dimer to a tetramer to a hexamer, suggesting the build-up of specific conformers as the length of the molecule increases. The CD spectrum of the hexamer shown in FIG. 6 is essentially identical with the published spectrum of the same one made by traditional amino acid couplings. Zhang, S., Prabpai, S., Kongsaeree, P., and Arvidsson, P. I. (2006). See Poly-N-methylated alpha-peptides: synthesis and X-ray structure determination of beta-strand forming foldamers, *Chemical communications* (Cambridge, England), 497-499. Thus, this chemistry provides a simple and efficient route to highly structured oligomers.

Example 9

A Combinatorial Library of Trimeric PTAs Via Solid-phase Sub-monomer Synthesis

Magnetic Beads Preparation: Magnetic beads (BioMag®Plus Carboxyl, Bangslabs inc, Fishers, Ind.) were first coated with protein L (ThermoScientific, Rockford, Ill.) using kit provided by Bangslabs.

On Bead Screening of PTA library against PX4-4: 0.5 g (approximately 250,000 beads) of the synthesized library on TENTAGEL was first swelled in DMF for 1 hour and washed thoroughly with 1×PBS five times and then equilibrated in 1×PBS overnight under mild shaking. The library was then washed again with PBS five times and then incubated with *e. coli* lysate in PBS with a total protein concentration at 1 mg/ml to block possible non-specific binding for 1 hour. The magnetic beads coated with protein L were then added to the blocking solution, made a final concentration of 1 mg magnetic beads/ml. The whole system was allowed for a further half hour incubation at room temperature with mild shaking. A rare earth 0.5 cm×0.5 cm×0.5 cm magnet was used to remove beads that bound to it, which were hits against protein L and magnetic beads. All magnetic beads were then removed by rare earth magnet and the beads were washed with 1×PBST five times. The library was then incubated with 5 ml of the blocking solution containing 2 mg/ml (total protein) *E. coli* lysate in 1×PBS. 10 mg of magnetic beads coated with protein L was then added to a 5 ml solution containing 20 µM of purified PX4-4 scFv and then incubated at room temperature for 0.5 hour. Then the two 5 ml solutions with library were combined together making a final concentration of 0.5 mg/ml magnetic beads, 10 µM PX4-4 scFv and 1 mg/ml (total protein) *E. coli* lysate. The whole system was incubated for another 1 hour with mild shaking. Hits were picked up from the system using rare earth magnets mentioned above, 33 hits were separated.

Hits Verification: All 33 beads were washed thoroughly and incubated with 1:300 trypsin at 37° C. for 1 hour, then washed with 1×PBST five times. The 33 beads were then incubated with 10 µM PX4-4 scFv for 1 hour and then a 1:200 dilution of Qdot655 (Invitrogen) conjugated with protein L in 1 ml of 1×PBS for 1 hour at room temperature, the beads were washed with 1×PBST three times and then put under fluorescence microscope (Olympus BX-51, DAPI filter) to examine for red halos surrounding them. If red halo did not appear, the bead was then excluded from the final hits identification. 17 hits were verified as true hits after Qdot verification.

Hits identification: All 17 hits were cleaved using CNBr and then characterized by MALDI mass spectrum. All 17 structures were resynthesized and examined against PX4-4 with FP assay. Only one hit was identified as binder with a Kd <10 µM.

Exemplary experimental procedures for Library synthesis with DIC: TENTAGEL beads (1 g, 160 µm, ~500,000 beads, 0.52 mmol/g, cat# HL 12 162, Rapp-Polymere GmbH, Germany) were swelled in DMF for 2 hours before use.

Figure 7:
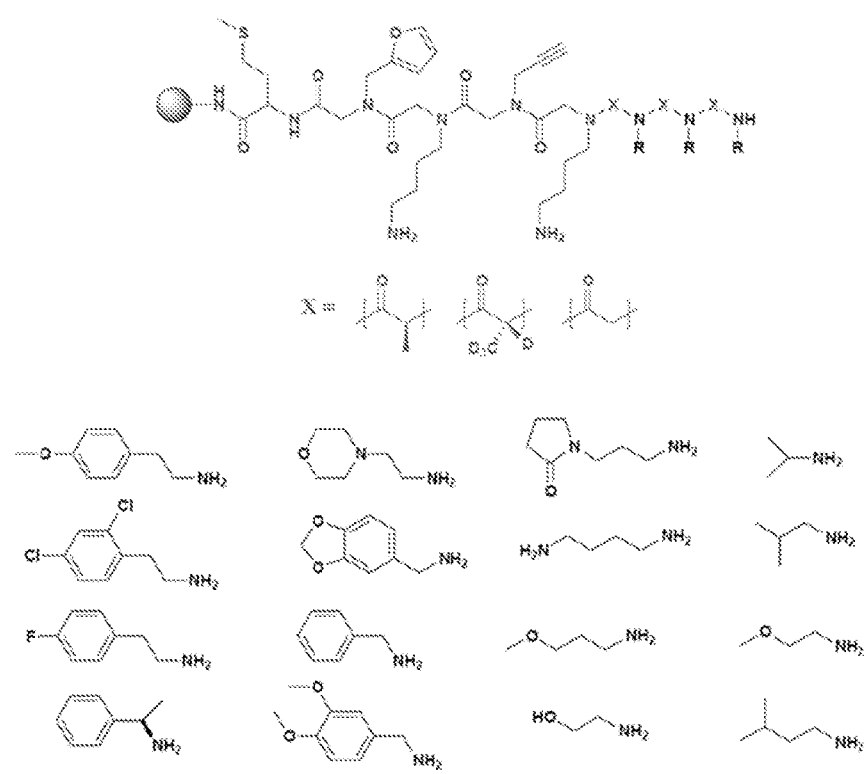
FIG. 7 shows structures of a combinatorial library of trimeric PTAs in accordance with some embodiments.

DMF was used as solvent unless otherwise mentioned. Fmoc-Met-OH (0.77 g, 2.08 mmol) was coupled on the beads using HBTU (0.77 g, 2.08 mmol), DIPEA (0.45 ml, 2.6 mmol). Fmoc was deprotected by 20% piperidine. Beads were washed thoroughly with DMF after each step. The beads were split in three portions after deprotection. 2 ml 1M DIC solution and 2 ml 1M corresponding bromoacid (2-bromo acid, (S)-2-bromopropanoic acid-d4 or (R)-2-bromopropanoic acid) solution were added together for preactivation for 5 min. The 4 ml combined solution was then added to one portion of beads and gently shook till completion. The reaction was monitored by chloranil test, a clear negative result after 5 min indicates the amine was acylated by the corresponding bromoacid. The beads was then thoroughly washed and pooled together, then split in 16 portions. Each portion was incubated with one of the amines listed in FIG. 7. 2M solution of the amine was used with an incubation time of 12 hours at 50° C. Silver acetate test and chloranil test were used to monitor the completion of the reaction. When reaction is complete, the beads were washed and pooled together. The acylation and amination steps were then repeated two more times for forming the trimer library.

In a chloranil test, 100 microliters of 2% chloranil solution in DMF is mixed with 100 microliters of 2% acetaldehyde in DMG before a test in a test tube. All the solutions are freshly prepared. The beads were dropped in the mixture and gently agitated. If the beads turned blue within five minutes, it indicated the presence of secondary amine on the surface of the beads.

In a silver acetate test, AgAc 50 mg was dissolved in 10 ml 0.5M acetic acid solution. Amine solution during the amination of PTA or peptoid were dropped in 0.3 ml of above solution and tested for AgBr precipitation. If AgBr precipitation formed, reaction was then allowed with fresh amine solution for an extended period of time till shown negative in silver acetate test which indicate none observable bromide were further replaced by amine during reaction.

Exemplary experimental procedures for Library synthesis with BTC: Tentagel beads with Rink linker (1 g, ~100,000 beads, 0.27 mmol/g, cat. # MB 250 230, Rapp-Polymere GmbH, Germany) was used in order to avoid long exposure to acid during cleavage. Beads were first treated by 20% piperidine in DMF in order to remove Fmoc and then the linker part is synthesized as described above. The beads was then split in three equal portions, coupled with 2-bromo acid, (S)-2-bromopropanoic acid-d4 and (R)-2-bromopropanoic acid respectively. For bromoacetic acid, 2M solution of DIC and 2M solution of bromoacetic acid were used as described above. For bromopropanoic acids, BTC was used as coupling reagent. BTC (92.1 mg, 0.31 mmol) was dissolved in 5 ml anhydrous THF in a glass vial. Bromopropionic acid (89 μl, 0.95 mmol) was then added to the vial and the whole vial was kept in −20° C. freezer for 15 min. Beads were washed using DCM, DMF and then THF respectively for 5 times each, then 2:1 THF/DIPEA (750 μl THF, 375 μl DIPEA, 2.2 mmol) was added to the beads and shook gently. 2,4,6-Trimethylpyridine (356 μl, 2.7 mmol), was added to the cold solution of bromopropionic acid with BTC, white precipitation was formed following the addition. The white suspension was then applied to the beads and the reaction vessel was put on shaker for 2 hours at room temperature. The solution in the vessel should be a pale yellowish suspension during the whole course of the reaction. A darker color is an indication of excessive heat released during the initial addition of the acid chloride solution. It can be solved by further cooling down the acid chloride solution and the beads. The beads were washed with DCM for five times when reaction was done and then DMF for 5 times. Chloranil test was used to monitor the completion of the reaction. All three portions of beads were then pooled together and the beads were incubated with 2M solution of the corresponding amine in DMF at 60° C. overnight. The completion of the reaction was monitored by chloranil and silver acetate test.

Synthesis and characterization of a combinatorial library: With the appropriate conditions in hand, the inventors proceeded to construct a combinatorial library of trimeric PTAs following an invariant linker. The synthesis was conducted on TENTAGEL beads, which is the preferred resin for subsequent screening. 2-bromo acid, (S)-2-bromopropanoic acid-$d_4$ and (R)-2-bromopropanoic acid) were employed as sub-monomers along with 16 amines (see FIG. 7). The theoretical diversity of the library was 110,592 compounds. The amines were chosen carefully such that any combination of amine and acid sub-monomers, when linked together, could be identified uniquely by tandem mass spectrometry. Methionine was added to the beads first using standard peptide coupling conditions (HBTU, Fmoc-Met-OH, DIEA) to facilitate selective release of the compounds from the beads after the screen by treatment with CNBr. Following the methionine, several invariant peptoid residues were added. The two Nlys residues facilitate display of the molecule in aqueous solution while the alkyne and furan side chains facilitate subsequent labeling of the compound and immobilization on a microarray if desired. Moreover, the additional mass serves to move the molecular ion and important fragment peaks out of the range of the matrix peaks, which facilitates compound characterization.

Following linker synthesis, the library was split in three, treated with DIC and (R)-2-bromopropanoic acid, (S)-2-bromopropanoic acid-$d_5$ or bromoacetic acid respectively. The beads were then mixed together and then split in 16 equal parts. One of the amines was added to each tube. The same procedures were then repeated three times in order to form the trimer. The acylation step was monitored by the chloranil test and the amine substitution was monitored by the silver acetate test (details are described in supplemental material). In addition, individual beads were sampled at each step. After releasing the compound using CNBr, the progress of the reaction was checked by MALDI mass spectrometry. This monitoring is important to create a high quality library. The acylation step in PTA synthesis, in particular, can be significantly slower than is the case for peptoid synthesis due to the greater degree of crowding around the nitrogen. Thus, while the conditions reported above for DIC-mediated coupling work well much of the time, this depends to some extent on the N-substituent. The blind use of a single set of reaction conditions without monitoring the reaction can result in a significant fraction of incomplete coupling.

In tubes where the reaction had not proceeded to >90% completion using the standard procedure, a second round of coupling was done by adding a 1M solution of 2:1 mixture of the bromopropanoic acid and DIC (after a pre-activation time of 10 minutes). Prolonged reaction time (24 hours) provides a satisfactory yield in these difficult reactions. With respect to assessing the progress of the reactions by mass spectrometry, the amide bond on the C-terminal side of the PTA fragments easily and is much more acid labile than in standard peptoids. This results in the production of an abundant b ion on the MALDI mass spectrum even without high energy MS/MS fragmentation.

After the final step, the entire library was washed thoroughly and 40 beads were picked randomly. The beads were treated with CNBr to release the compounds from the beads, which were then analyzed by tandem MALDI mass spectrometry. 37 out of 40 beads were sequenced successfully. All 16 of the amines and all three of the acids were found in these spectra, suggesting that all of the sub-monomers had incorporated in this synthesis. However, the inventors observed no trimers in which a methyl group was present at all three positions and some dimers were also found. The demanding library synthesis format, the reaction conditions employed might have resulted in some level of failure when attempting to string together three chiral centers in a row, despite all of our efforts. As described below, a modified coupling protocol solved this problem. Nonetheless, since most compounds in the library could be sequenced, the inventors decided to proceed with a screening experiment to probe the idea that the greater conformational constraints in the PTA relative to peptoids might result in higher affinity ligands.

Isolation and characterization of protein ligands from the PTA library: The library shown in FIG. 7 was screened for ligands to a single chain variable fragment (scFv) antibody called PX4-4, which was derived from a patient with the skin blistering disease Pemphigus vulgaris. See Yamagami, J., Payne, A. S., Kacir, S., Ishii, K., Siegel, D. L., and Stanley, J. R., Homologous regions of autoantibody heavy chain complementarity-determining region 3 (H-CDR3) in patients with pemphigus cause pathogenicity, *The Journal of clinical investigation* 120, 4111-4117 (2010). Approximately 250,000 beads were incubated with 10 µM of purified scFv PX4-4 in the presence of 1 mg/ml *E. coli* lysate as a diverse source of competitor proteins. To isolate beads that display ligands that captured significant amounts of the target antibody, magnetic beads displaying protein L were added to the mixture. Protein L will bind tightly to the scFv antibody through the variable region of the kappa light chains. After a brief incubation, a powerful magnet was employed to segregate the beads that had also affixed to the magnetic protein L-displaying beads. 33 beads were isolated as possible hits.

To confirm that these beads were true hits, they were stripped of protein by incubation in a trypsin solution at 37° C. for one hour, then washed thoroughly. The beads were then incubated with 10 µM of purified scFv PX4-4 again for 30 minutes and washed gently. A 1:200 dilution of red quantum dots conjugated to protein L was then added. After 30 minutes of incubation, brightly glowing beads were picked manually using a low power fluorescence microscope to visualize them. 17 of the hits picked up magnetically displayed a red glow (not shown), consistent with their being PX4-4 ligands. These validated hits were released from the beads with CNBr and sequenced by tandem mass spectrometry.

Figure 8A:
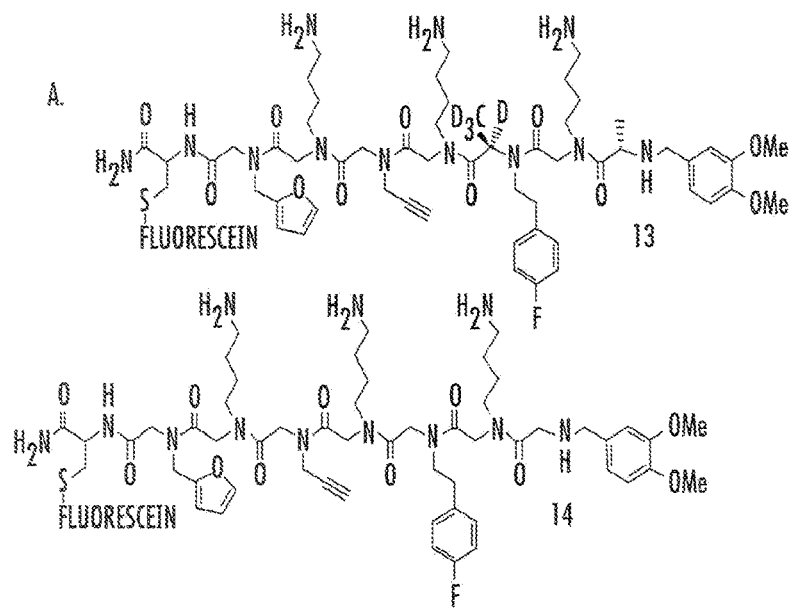
FIG. 8A-8B show structure and characterization of a ligand for the scFv PX4-4.

The most promising hit from the bead screen (as judged by the intensity of the red halo after quantum dot addition), compound 13, was re-synthesized on Rink amide resin with a fluorescein tag, cleaved and purified by HPLC. FIG. 8A shows structures of a fluoroscein-labeled derivative of one of the screening hits 13 and the peptoid analogue 14, which lacks the methyl groups at the chiral center. As shown in FIG. 8A, this compound proved to have chiral centers at the first and third variable positions of the library, whereas there was no Cα substituent at the second position.

Figure 8B:
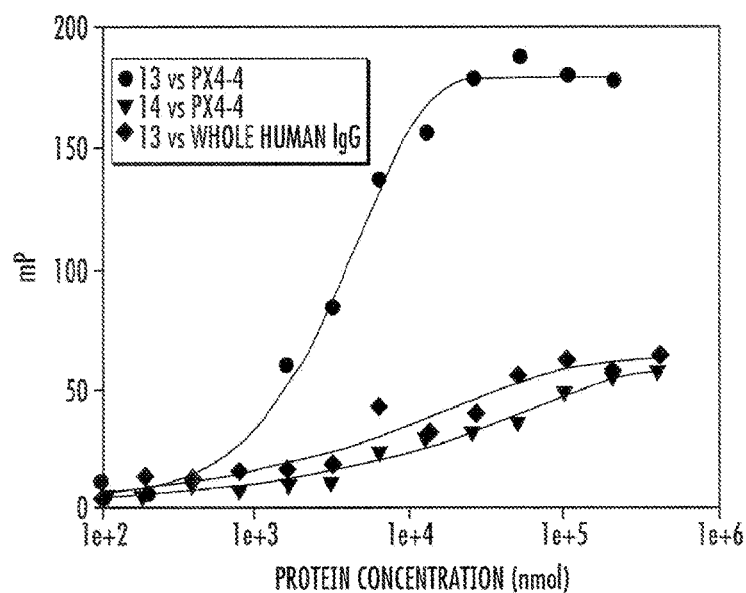

The affinity of compound 13 for PX4-4 was determined by fluorescence anisotropy. As shown in FIG. 8B, PTA fluorescein-conjugated 13 exhibited a saturable binding curve when titrated with increasing concentrations of PX4-4, indicating a $K_D$ of approximately 5 µM. In contrast, little binding was observed when fluorescein-tagged 13 was mixed with bulk IgG antibodies, indicating selectivity for PX4-4.

The peptoid analogue of 13, compound 14, which lacks any chiral centers, was also made. As shown in FIG. 8B, this compound had a much lower affinity for PX4-4. The large difference in affinity of PTA 13 and peptoid 14, which differ only in the presence or absence of the methyl groups at the chiral centers, is striking. While we cannot rule out the possibility that the Cα methyl groups in PTA 13 contact the scFv antibody directly, these data strongly support the idea that the conformational constraints afforded by the presence of the chiral centers strongly stabilizes binding of the small molecule to the antibody fragment.

To more thoroughly probe the influence of the stereochemistry at each position of PTA 13, we decided to synthesize a small library in which the amines were held invariant as found in 13, but all possible combinations of the three acid sub-monomers were employed at each position. In order to ensure the efficient synthesis of PTA trimers, the inventors performed an extensive optimization of acylation conditions as well as conditions for amination. Of the eight coupling reagents examined, the triphosgene reagent bis (trichloromethyl) carbonate (BTC) was preferred, providing superior yields with no racemization.

Several beads were chosen randomly from the library, and the compounds were released and analyzed by mass spectrometry. Gratifyingly, in this case, several of the compounds were trimers with chiral centers at each position. Indeed, close to the expected ratio of compounds was observed, demonstrating that the use of the BTC-based protocol is appropriate for the synthesis of high quality PTA libraries.

Figure 9A:
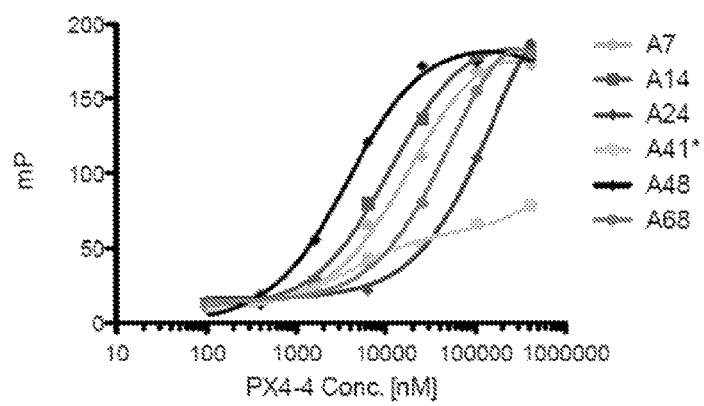
FIG. 9A-9B show binding isotherm for A48 (also known as compound 13) and five other highest affinity members of the library in which the stereochemistry at each alpha-carbon of 3 was altered.
Figure 9B:
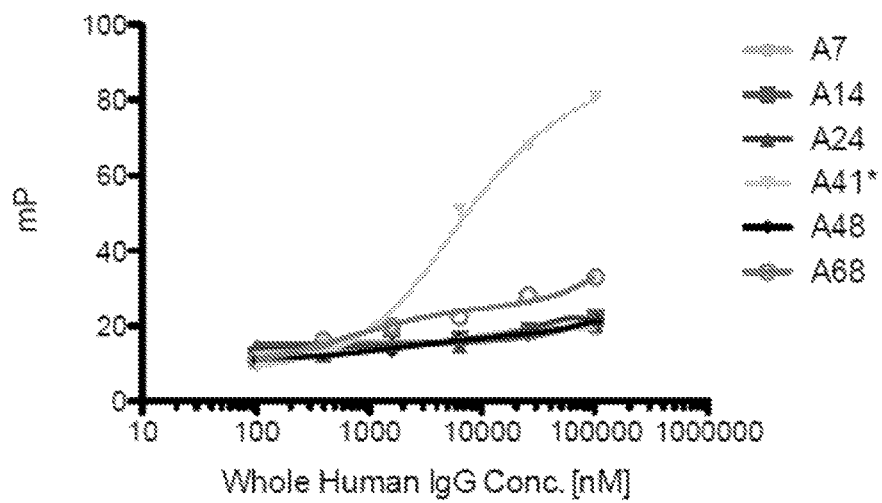

96 beads were chosen randomly from the library and placed individually into the wells of a 96-well filter plate. Each well was treated with fluorescein azide and a copper catalyst to attach fluorescein to the alkyne handle and then the compounds were cleaved from beads. The beads were filtered out and the soluble compounds were used for the fluorescence polarization (FP) assay. All 27 possible structures were found in this collection of molecules by tandem MS sequencing. Semi-quantitative binding constants for the PX4-4 antibody all 27 of the compounds were determined by titrating the compounds with the protein in the microwell format and monitoring the increase in FP. The six highest affinity compounds, which included A48 (also known as compound 13), identical to hit 14 in the variable region, were re-synthesized and purified to allow more accurate binding data to be acquired. All six compounds showed an increase in FP when titrated with PX4-4. Most of the curves approached saturation, allowing for an accurate determination of the $K_D$. In contrast, compound A41, corresponding to peptoid 14, was not saturated in the tested protein concentration range (100 nM to 400 µM) (FIG. 9B). The results are summarized in Table 1.

These data confirmed that compound 13 is the highest affinity PX4-4 ligand of the six and that the stereochemistry of the chiral centers can have a profound effect on binding affinity. The compounds with the S,S,R or S,R,S configurations (the same as compound 13 in the first and third positions, but with a chiral center at position 2) were not high affinity ligands for PX4-4. This indicates that a stereocenter at the second position does not allow the molecule to access the bound conformation.

To address the selectivity of compounds A14 (N,R,S configuration), A7 (N,S,S), A68 (R,S,R), A41(N,N,N) and A24 (R,R,R) for PX4-4, the FP experiment was repeated using a mixture of human IgG as we did previously for compound 13. A14, A7, A68 and A24 showed no binding with whole human IgG while A41, the analogue of peptoid 14, had a similar affinity for these random antibodies as it did for PX4-4 (FIG. 9B). This implies that greater conformational flexibility is associated with binding promiscuity.

TABLE 1

Kd values of six compounds having high affinity with PX4-4

| No. | 1 | 2 | 3 | Kd-96 | std. dev. | Kd-re |
|-----|---|---|---|-------|-----------|-------|
| A48 | S | N | R | 22.6  | ±10.5     | 6.7   |
| A14 | N | R | S | 27.5  | ±4.5      | 19.1  |
| A7  | N | S | S | 40.9  | N/A       | 25.4  |
| A68 | R | S | R | 43.2  | N/A       | 65.2  |
| A41 | N | N | N | 113.4 | ±9.3      | NA    |
| A24 | R | R | R | 116.8 | ±20.1     | 233   |

All patents, patent applications and publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof. All such modifications are intended to be encompassed within the below claims of the invention.

What is claimed is:

1. A process for preparing a peptide tertiary amide of formula (I) or its enantiomer with the opposite stereochemistry at Cα:

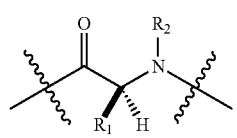

(I)

wherein $R^1$ is selected from optionally substituted $C_1$-$C_{10}$ alkyl, optionally substituted aryl, optionally substituted alkaryl, optionally substituted alkoxyl, optionally substituted heteroaryl, arylalkoxyl, optionally substituted acyl, OH, OR', $NH_2$, NHR', $NR'_2$, SH, SR', C(O)R', and an amino acid side chain;

$R^2$ is selected from optionally substituted $C_2$-$C_{10}$ alkyl, optionally substituted aryl, optionally substituted alkaryl, optionally substituted alkoxyl, optionally substituted heteroaryl, arylalkoxyl, optionally substituted acyl, OH, OR', $NH_2$, NHR', $NR'_2$, SH, SR', C(O)R', and an amino acid side chain;

wherein

R' is selected from optionally substituted $C_1$-$C_{10}$ alkyl, optionally substituted $C_1$-$C_{10}$ alkenyl, optionally substituted $C_1$-$C_{10}$ alkynyl, optionally substituted aryl, optionally substituted alkaryl, and optionally substituted acyl;

comprising:

oxidizing a primary amine of an amino acid of formula (II)

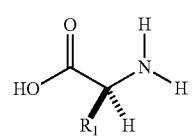

(II)

with an oxidizing agent followed by treatment with a nucleophilic bromide source to give an optically pure 2-bromo acid of formula (III):

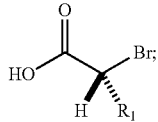 (III)

wherein the synthesis further comprises a solid or semi-solid phase synthetic step
wherein the solid or semi-solid phase synthetic step comprises bonding the 2-bromo acid of formula (III)

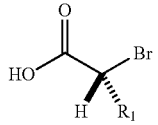 (III)

to the solid-phase bead using a coupling agent in a solvent to give a compound of formula (V)

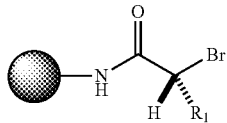 (V)

wherein the compound of formula (V) is reacted with an amine of formula (IV)

 (IV)

to give a compound of formula (VI):

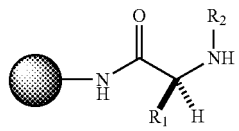 (VI)

and wherein the compound of formula (VI) is further reacted with additional 2-bromo acid of formula (III) followed by an amine of formula (IV) to obtain oligomers of the compound of formula (VI).

2. The process of claim 1, wherein the oxidizing agent comprises one of nitrous acid and sulfuric acid.

3. The process of claim 1, wherein the bromide source comprises a chemical selected from the group consisting of potassium bromide, hydrogen bromide, and sodium bromide.

4. The process of claim 1, wherein the amine of formula (IV) is a primary amine.

5. The process of claim 1, wherein the peptide tertiary amide comprises at least 90% enantiomeric excess of the (R) enantiomer.

6. The process of claim 1, wherein the peptide tertiary amide comprises at least 90% enantiomeric excess of the (S) enantiomer.

7. The process of claim 1, wherein the peptide tertiary amide comprises one or more Cα- and N-substitutions.

8. The process of claim 1, wherein the solid-phase comprises a bead.

9. The process of claim 8, wherein the solid-phase comprises a bead having a methionine linker.

10. The process of claim 1, wherein the solvent is N,N-dimethylformamide.

11. The process of claim 1, wherein the oligomers of the compound of formula (VI) are released from the bead by cleaving the oligomers from the solid-phase bead by reacting the bound oligomer with cyanogen bromide.

* * * * *